US012059520B2

(12) United States Patent
Zafiris

(10) Patent No.: US 12,059,520 B2
(45) Date of Patent: Aug. 13, 2024

(54) PRIMING SENSOR FOR A MEDICAL FLUID DELIVERY SYSTEM

(71) Applicants: BAXTER INTERNATIONAL INC., Deerfield, IL (US); BAXTER HEALTHCARE SA, Glattpark (CH)

(72) Inventor: John Zafiris, Hawthorn Woods, IL (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 428 days.

(21) Appl. No.: 16/839,602

(22) Filed: Apr. 3, 2020

(65) Prior Publication Data

US 2020/0316280 A1 Oct. 8, 2020

Related U.S. Application Data

(60) Provisional application No. 62/830,906, filed on Apr. 8, 2019.

(51) Int. Cl.
*A61M 1/28* (2006.01)
*A61M 1/14* (2006.01)
*A61M 1/16* (2006.01)

(52) U.S. Cl.
CPC .......... *A61M 1/288* (2014.02); *A61M 1/159* (2022.05); *A61M 1/1645* (2014.02); *A61M 1/166* (2014.02); *A61M 1/282* (2014.02); *A61M 1/1561* (2022.05); *A61M 2205/3396* (2013.01)

(58) Field of Classification Search
CPC .... A61M 1/288; A61M 1/1645; A61M 1/166; A61M 1/282; A61M 2205/3396; A61M 1/28; A61M 2205/14; A61M 2205/3306; A61M 1/3643; A61M 2205/331; A61M 2205/502
See application file for complete search history.

(56) References Cited

U.S. PATENT DOCUMENTS

2016/0101278 A1* 4/2016 Norris .................. A61M 39/22
604/29

OTHER PUBLICATIONS

Written Opinion of PCT/US2020/026842 mailing dated Feb. 24, 2021—6 pages.
IPRP of PCT/US2020/026842 mailing dated Jul. 16, 2021—21 pages.

* cited by examiner

*Primary Examiner* — Krishnan S Menon
(74) *Attorney, Agent, or Firm* — K&L Gates LLP

(57) ABSTRACT

A priming sensor for a medical fluid delivery device is disclosed. In an example, the priming sensor includes light emitters and a detector. The detector is configured to detect light emitted by the emitters that interacts with a patient tube connected to the priming sensor. A processor of a medical fluid delivery device causes the emitters to operate in a sweep pattern during a sweep period. The processor receives output data from the detector that is indicative of light detected during the sweep period. The processor creates an output waveform corresponding to the sweep period based on the output data and compares the output waveform to at least one reference waveform to determine one of (a) a no-tube state, (b) a dry tube state, or (c) a wet tube state. The processor provides an output indicative of the comparison for operation of the medical fluid delivery device.

17 Claims, 25 Drawing Sheets

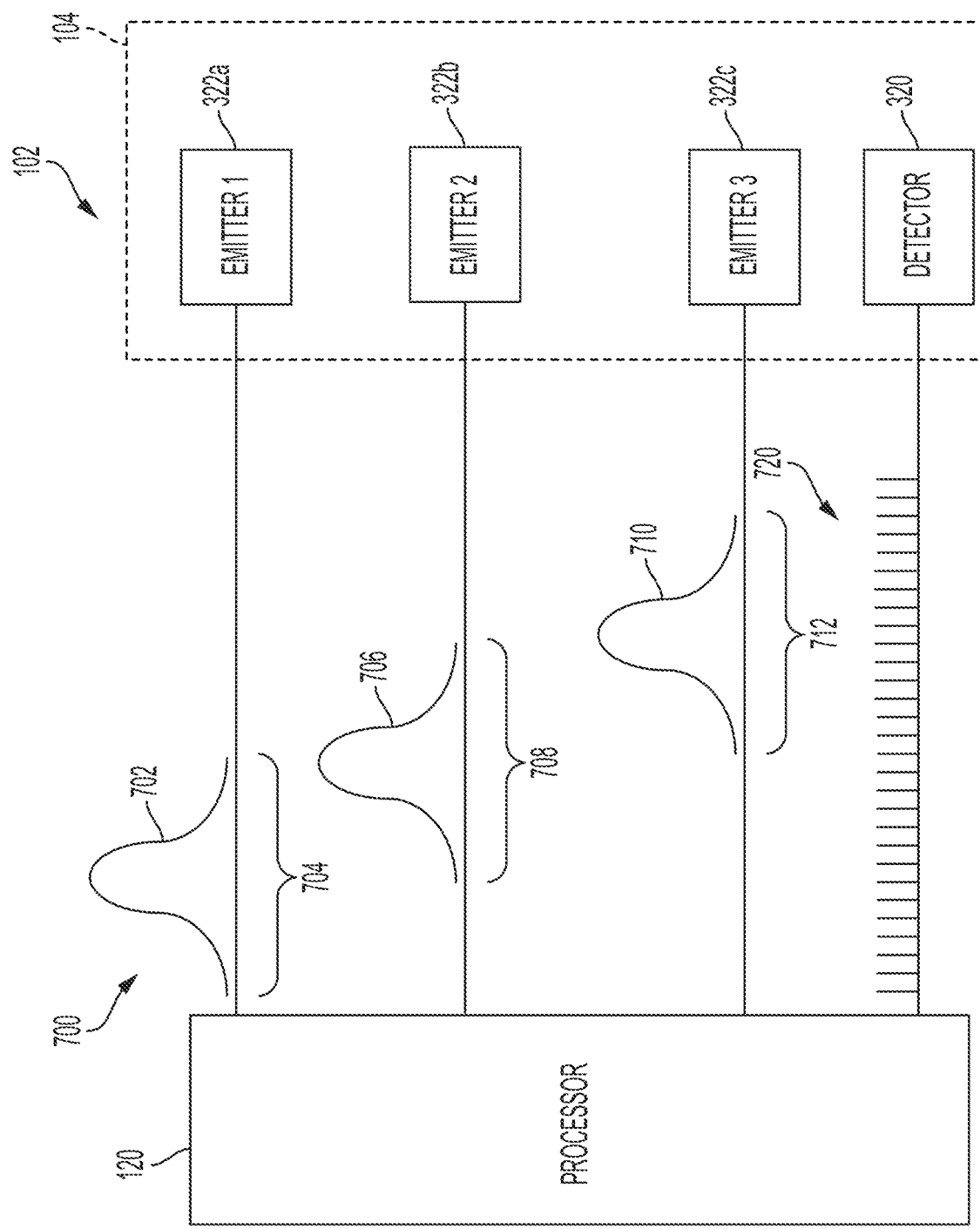

PRIMING SENSOR FOR A MEDICAL FLUID DELIVERY SYSTEM

PRIORITY CLAIM

This application claims priority to and the benefit of U.S. Provisional Patent Application Ser. No. 62/830,906, filed on Apr. 8, 2019, the entire disclosure of which is hereby incorporated by reference.

BACKGROUND

People with damaged or improperly functioning kidneys may undergo dialysis treatments to remove waste products from blood. One common type of dialysis is peritoneal dialysis ("PD"), in which a cleansing fluid, referred to as peritoneal dialysis fluid, is moved into a patient's peritoneal cavity of their abdomen via a catheter. The cleansing fluid absorbs waste products during a dwell period. After the dwell period has ended, the cleansing fluid is removed from the patient's peritoneal cavity with the absorbed waste products, thereby compensating for the patient's damaged kidneys.

Oftentimes, a PD machine is used to pump a prescribed volume of the cleansing fluid into the patient's peritoneal cavity. The PD machine permits the cleansing fluid to remain in the patient during the dwell period. After the dwell period, the PD machine drains the cleansing fluid, with the waste products, from the patient's peritoneal cavity. Certain PD machines typically prime tubes and tubing sets that route the cleansing fluid to the patient to remove air, thus preventing air from being transmitted into a patient's peritoneal cavity. Priming typically involves pumping the cleansing fluid to an end of a tube, such as a tube that is connected to the patient during the PD therapy, to remove the air within the tube.

PD machines may be located in a patient's home, a clinic, or a hospital. Many times, a patient prepares their machine for treatment, including running a priming sequence. To help a patient prime the tubes, PD machines may include a sensor that detects when a tube is properly primed. Certain sensors use light to detect when cleansing fluid has reached the end of a tube, which is indicative of a successful prime. However, fluctuations in ambient light, tube properties, and/or fluid type may cause a light sensor to be less accurate than desired.

SUMMARY

The example system, apparatus, and method disclosed herein are configured to provide an accurate dialysis priming sensor that is relatively insensitive to ambient light brightness, tube properties, and/or fluid type. The dialysis priming sensor includes at least two light emitters and at least one light detector. A processor is configured to activate the at least two light emitters in a sweeping pattern, while sampling an output from the at least one light detector during a priming sequence for a PD machine. The example processor is configured to compare the data from the sampled output to one or more reference curves to detect when no tube is present, when a tube is present but dry, or when a tube is present and includes a fluid (such as a priming fluid). The processor is further configured such that after detecting that a tube is present and includes a fluid (e.g., a wet tube state), the processor provides an indication that priming of a patient line for PD is successful and permits a priming sequence to continue/end and/or a PD treatment to begin. The processor may also be configured to provide an indication of a failed prime of the patient line if, for example, the wet tube state is not detected within a defined period of time.

The example system, apparatus, and method, in an embodiment, perform a sweeping pattern with light emitters for performing an analysis based on transmissive and reflective light caused by the light interacting with the tube and any fluids in the tube. The emitters may be positioned at different angles with respect to the tube and a detector to differentiate light transmission and reflectance for each emitter to create variability in the sweep pattern. During a sweep, a light detector is sampled between ten and one hundred times, for example, and in one preferred embodiment between fifty and seventy-five times. The example system, method, and apparatus are configured to use the sampled light brightness data to create a waveform of detected light brightness during the sweep period. Different waveform patterns are formed based upon whether a tube is present and whether or not fluid resides inside the tube. The example system, method, and apparatus use different reference waveforms for comparison to a detected or sampled waveform to determine whether a tube is present and whether a present tube contains a fluid. The differences between the waveform shapes for each of the different possible tube states eliminate potential detection errors caused by varying ambient light conditions, tube properties, and/or fluid properties.

In light of the disclosure herein and without limiting the disclosure in any way, in a first aspect of the present disclosure, which may be combined with any other aspect listed herein unless specified otherwise, a peritoneal dialysis apparatus includes a patient tube configured to receive dialysis fluid from a source of dialysis fluid, at least one pump configured to move dialysis fluid from the source to the patient tube, a priming sensor including a first emitter, a second emitter, a third emitter, and a detector, the detector configured to detect light emitted by the first emitter, the second emitter, and the third emitter that interacts with or passes through the patient tube, a processor configured to operate the priming sensor, and a memory storing instructions, which when executed by the processor, cause the processor to (i) cause the first emitter, the second emitter, and the third emitter to operate in a sweep pattern during a sweep period, where a peak brightness of the first emitter occurs before a peak brightness of a second emitter, and the peak brightness of the second emitter occurs before a peak brightness of the third emitter, (ii) receive output data from the detector that is indicative of light detected during the sweep period, (iii) create an output waveform corresponding to the sweep period based on the output data, (iv) compare the output waveform to at least one reference waveform to determine one of (a) a no-tube state, (b) a dry tube state, or (c) a wet tube state, and (v) provide an output indicative of the comparison.

In accordance with a second aspect of the present disclosure, which may be used in combination with any other aspect listed herein unless stated otherwise, the processor is further configured such that if the wet tube state is determined, a message indicative of the wet tube state is transmitted, and (i) to (iv) are repeated during a priming sequence while the least one pump is caused to move the dialysis fluid from the source to the patient tube until the wet tube state is determined.

In accordance with a third aspect of the present disclosure, which may be used in combination with any other aspect listed herein unless stated otherwise, the processor is further configured such that if the wet tube state is determined, a peritoneal dialysis treatment is enabled.

In accordance with a fourth aspect of the present disclosure, which may be used in combination with any other aspect listed herein unless stated otherwise, the processor is configured to determine an analytical output waveform by calculating a derivative of the output waveform, and compare the analytical output waveform to the at least one reference waveform to determine one of the states (a) to (c).

In accordance with a fifth aspect of the present disclosure, which may be used in combination with any other aspect listed herein unless stated otherwise, the apparatus includes at least three reference waveforms, and the processor is configured to match one of the reference waveforms to the output waveform to determine the states (a) to (c).

In accordance with a sixth aspect of the present disclosure, which may be used in combination with any other aspect listed herein unless stated otherwise, the apparatus includes a user interface configured to display at least one of text or a graphic corresponding to the determined state (a) to (c).

In accordance with a seventh aspect of the present disclosure, which may be used in combination with any other aspect listed herein unless stated otherwise, the processor and the detector cooperate to acquire between ten and one-hundred samples to form the output data indicative of the detected light during the sweep period.

In accordance with an eighth aspect of the present disclosure, which may be used in combination with any other aspect listed herein unless stated otherwise, the processor is configured to increment a counter each time the wet tube state is determined, compare a value of the counter to a counter threshold, and determine the wet tube state when the value of the counter equals or exceeds the counter threshold.

In accordance with a ninth aspect of the present disclosure, which may be used in combination with any other aspect listed herein unless stated otherwise, the counter threshold is between two and ten.

In accordance with a tenth aspect of the present disclosure, which may be used in combination with any other aspect listed herein unless stated otherwise, the processor causes the emitters to operate in the sweep pattern by at a first time, causing the first emitter to emit light during a first time period according to an activation pattern that is defined by instructions in the memory, at a second time after the first time, causing the second emitter to emit light during a second time period according to the activation pattern, and at a third time after the second time, causing the third emitter to emit light during a third time period according to the activation pattern.

In accordance with an eleventh aspect of the present disclosure, which may be used in combination with any other aspect listed herein unless stated otherwise, the second time begins during the first time period or after the first time period, and the third time begins during the second time period or after the second time period.

In accordance with a twelfth aspect of the present disclosure, which may be used in combination with any other aspect listed herein unless stated otherwise, the second time begins between halfway through and ¾ of the way through the first time period, and the third time begins between halfway through and ¾ of the way through the second time period.

In accordance with a thirteenth aspect of the present disclosure, which may be used in combination with any other aspect listed herein unless stated otherwise, the activation pattern specifies a control of a brightness of the light emitted by the first, second, and third emitters by increasing a duty cycle from a start of a respective time period until half of the respective time period where the peak brightness is reached, and decreasing the duty cycle from half of the respective time period until the end of the respective time period.

In accordance with a fourteenth aspect of the present disclosure, which may be used in combination with any other aspect listed herein unless stated otherwise, the activation pattern corresponds to a Gaussian impulse waveform.

In accordance with a fifteenth aspect of the present disclosure, which may be used in combination with any other aspect listed herein unless stated otherwise, the first emitter is located on a first side of the patient tube opposite from the detector which is located on a second side of the patient tube when the patient tube is inserted into the priming sensor.

In accordance with a sixteenth aspect of the present disclosure, which may be used in combination with any other aspect listed herein unless stated otherwise, the second emitter is located on the first side of the patient tube adjacent to the first emitter, and the third emitter is located adjacent to the second emitter and is aligned to direct light between 30 and 60 degrees relative to light emitted from the first emitter and the second emitter.

In accordance with a seventeenth aspect of the present disclosure, which may be used in combination with any other aspect listed herein unless stated otherwise, the first emitter is positioned to be a transmissive light emitting diode relative to the detector, the second emitter is positioned to be an intermediate light emitting diode relative to the detector, and the third emitter is positioned to be a reflective light emitting diode relative to the detector.

In accordance with an eighteenth aspect of the present disclosure, which may be used in combination with any other aspect listed herein unless stated otherwise, the priming sensor includes at least one retainer section configured to retain the patient tube within the priming sensor.

In accordance with a nineteenth aspect of the present disclosure, which may be used in combination with any other aspect listed herein unless stated otherwise, a peritoneal dialysis apparatus includes a priming sensor including a first emitter, a second emitter, and a detector, the detector configured to detect light emitted by the first emitter and the second emitter through a dialysis tube, a processor configured to operate the priming sensor, and a memory storing instructions, which when executed by the processor, cause the processor to cause the first emitter and the second emitter to operate in a sweep pattern during a sweep period, receive output data from the detector that is indicative of light detected during the sweep period, create an array curve corresponding to the sweep period based on the output data, determine a state of the dialysis tube based on the array curve, the state including at least one of a no-tube state, a dry tube state, and a wet tube state, and if the wet tube state is determined, transmit a message indicative that the dialysis tube is primed.

In accordance with a twentieth aspect of the present disclosure, which may be used in combination with any other aspect listed herein unless stated otherwise, the processor is configured to determine the state of the dialysis tube by removing common-mode offsets of the array curve to exclude ambient light effects, scaling the array curve based on the common mode offset to normalize a shape of the array curve, computing a first derivative of the scaled array curve, subtracting a reference curve for each of the three states from the first derivative of the scaled array curve, calculating an absolute value of an area for each of the three reference curves by subtracting the respective reference curve from the scaled array curve, and determining the state by selecting the reference curve that corresponds to a smallest absolute value of the area for the reference curve.

In a twenty-first aspect of the present disclosure, any of the structure, functionality, and alternatives disclosed in connection with any one or more of FIGS. 1 to 28 may be combined with any other structure, functionality, and alternatives disclosed in connection with any other one or more of FIGS. 1 to 28.

In light of the present disclosure and the above aspects, it is therefore an advantage of the present disclosure to provide an improved priming system, device, and method for a medical fluid delivery system.

It is another advantage of the present disclosure to accurately detect when a fluid reaches a certain position within a dialysis tube regardless of ambient light, tube properties, and/or fluid properties.

It is yet another advantage of the present disclosure to provide a priming sensor and methodology that may be applied to different types of medical fluid delivery machines.

The advantages discussed herein may be found in one, or some, and perhaps not all of the embodiments disclosed herein. Additional features and advantages are described herein, and will be apparent from, the following Detailed Description and the figures.

BRIEF DESCRIPTION OF THE FIGURES

FIGS. 7A to 7E are diagrams that illustrate how a processor operates with the priming sensor of FIGS. 3 and 4 to create a sweep pattern, according to an example embodiment of the present disclosure.

DETAILED DESCRIPTION

Figure 1:
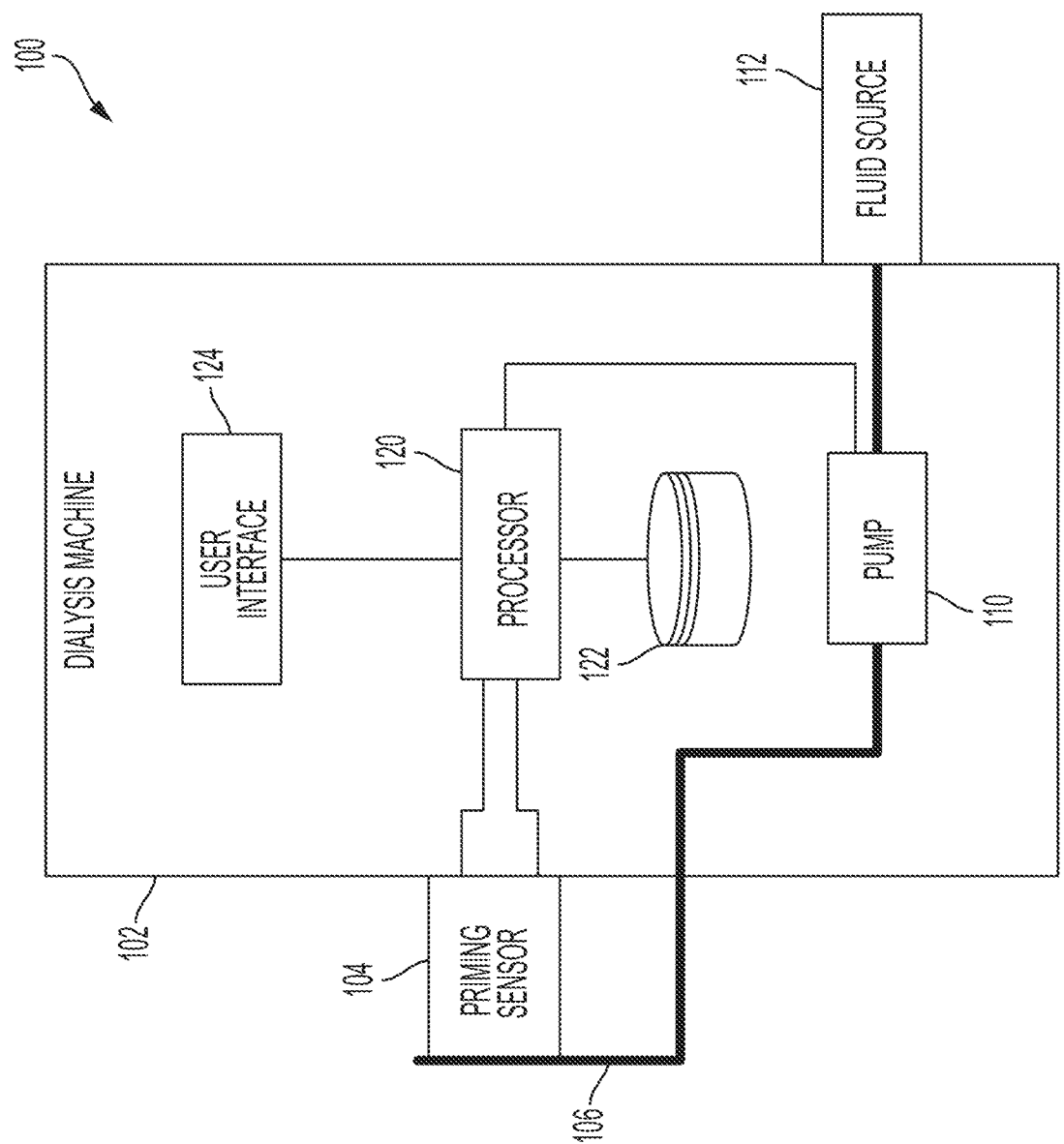
FIG. 1 is a schematic view illustrating a diagram of an example medical fluid delivery system including a priming sensor and a dialysis machine, according to an example embodiment of the present disclosure.

A medical fluid delivery system is disclosed herein. The example medical fluid delivery system may include a peritoneal dialysis machine and/or a hemodialysis machine. The medical fluid delivery system includes a priming sensor configured to detect when at least one tube or line set is primed with an appropriate fluid, such as a clean or priming liquid. The priming sensor includes a plurality of light emitters and at least one light detector. During a priming operation, the light emitters are activated in a sweeping pattern, while the detector records periodic samples of light brightness. The sampled data is aggregated or otherwise combined into a waveform (e.g., an array curve) that is indicative of detected light brightness over the sweep period. The waveform is compared to reference waveforms that correspond to different possible states including, for example, a no-tube state, a dry tube state, and a wet tube state. The closest reference waveform to the detected waveform is selected to determine the current state of priming associated with the dialysis tube.

In some examples, the medical fluid delivery system is configured such that if the no-tube state is detected, the medical fluid delivery system provides an alert indicative that the dialysis tube needs to be inserted into the priming sensor. The medical fluid delivery system may prevent priming of the dialysis tube from starting until the tube is detected by the sensor. If a dry tube state is detected, the medical fluid delivery system may begin and/or continue a priming sequence by pumping a fluid from a fluid source into the dialysis tube. If a wet tube state is detected, the medical fluid delivery system may stop pumping the fluid from the fluid source and/or end the priming sequence. In some embodiments, the medical fluid delivery system may be configured to detect the wet tube state multiple times (e.g., between two and ten times to ensure the proper result is validated) before priming ends.

The example system, method, and apparatus provide an improvement over known priming sensors that detect a tube state using light. Currently, light-based priming sensors activate all of the light emitters at the same time or activate each emitter separately. The emitters are activated to have the same brightness level. If all of the emitters are activated at the same time, the detected light is compared to different thresholds, where the state is determined based on which thresholds are exceeded. If the emitters are activated individually, the detected light from each emitter is compared to a separate threshold (or combined into a ratio and compared to a threshold), where a tube state is determined based on a weighted average of the thresholds exceeded.

Both of these known detection methods can be inaccurate as a result of ambient light affecting the detection of light emitted by the emitters. These known tube detection methods are based on light detected, with comparisons being made to absolute static thresholds. Increases in ambient light cause the amount of light detected by a light sensor to increase, thereby creating errors associated with tube detection. Similar errors can be introduced based on tube properties (e.g., tube thickness, tube composition, material transparency/reflectivity, light absorption, tube diameter) and fluid properties (e.g., viscosity, density, turbidity/transparency, color, light absorption).

In contrast to known methods, the example system, method, and apparatus disclosed herein, in an embodiment, activates light emitters in a sweeping pattern. During the sweeping pattern, the brightness of light transmitted by the emitters is changed over time and at least some of the emitters may be activated at the same time. The use of a sweeping pattern creates one or more unique waveforms for each possible detection state, thereby providing anti-aliasing. The difference between the waveforms for each of the different tubes states is significant and repeatable. Additionally, the significant difference between the waveforms of different tube states prevents or reduces variability due to ambient light, tube properties, fluid properties, hardware, and/or signal noise from affecting tube state detection. The significant difference between the waveforms also enables the priming sensor of the present disclosure to be provisioned without calibration for different ambient light conditions, tube properties, and/or fluid properties. The example system, method, and apparatus disclosed herein accordingly provide improved priming state detection for a dialysis tube.

The example disclosure refers to peritoneal dialysis and priming a patient tube. It should be appreciated that the example system, apparatus, and method disclosed herein can be provided to operate with any type of dialysis machine, including a hemodialysis machine or a continuous replacement treatment machine. Moreover, the improved priming sensing discussed herein is not limited to dialysis, and may be used with any type of medical fluid machine, such as a medical delivery machine (e.g., an infusion pump). Further, while the disclosure relates to a patient tube, in other examples, other tubes may be primed using a priming sensor, such as a heating tube, a drain tube, a source tube, etc. Further, while the disclosure references priming a tube using dialysate or dialysis fluid, it should be appreciated that the example system, apparatus, and method may operate with any type of fluid, including saline, renal therapy fluid, blood, sterile water, etc. Additionally, the improved sensing may be used for any purpose in which it is desired to know whether a tube is present or not and it so, whether the tube contains a liquid.

Dialysis System Embodiment

Referring now to the drawings, FIG. 1 illustrates an example medical fluid delivery system 100, according to an example embodiment of the present disclosure. The medical fluid delivery system 100 in the illustrated embodiment includes a dialysis machine 102 configured to provide renal failure therapy to one or more patients. Renal failure therapy helps a patient balance water and minerals. Renal failure therapy also helps excrete daily metabolic load by removing a patient's toxic end products of nitrogen metabolism (urea, creatinine, uric acid, and others), which accumulate in blood and tissue. Renal failure therapy for the replacement of kidney function is critical to many people because the treatment is lifesaving.

In some examples, the dialysis machine 102 is a peritoneal dialysis ("PD") machine. Here, the dialysis machine 102 is configured to infuse a dialysis solution, also called dialysis fluid or renal failure therapy fluid into a patient's peritoneal cavity via a catheter. The dialysis fluid contacts the peritoneal membrane of the peritoneal cavity for a period of time, referred to as a dwell period. Waste, toxins and excess water pass from the patient's bloodstream, through the peritoneal membrane and into the dialysis fluid due to diffusion and osmosis, i.e., an osmotic gradient occurs across the membrane. An osmotic agent in dialysis provides the osmotic gradient. The used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), and tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal cavity. The patient then connects the catheter to a bag of fresh dialysis fluid to infuse fresh dialysis fluid through the catheter and into the patient. The patient disconnects the catheter from the fresh dialysis fluid bag and allows the dialysis fluid to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, such as the dialysis machine 102, however, perform the cycles automatically, typically while the patient sleeps. APD machines free patients from having to perform the treatment cycles manually and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal cavity. APD machines also allow for the dialysis fluid to dwell within the cavity and for the transfer of waste, toxins and excess water to take place. The source may include multiple sterile dialysis fluid bags.

APD machines pump used or spent dialysis fluid from the peritoneal cavity, though the catheter, and to the drain. As with the manual process, several drain, fill and dwell cycles occur during dialysis. A "last fill" occurs at the end of APD and remains in the peritoneal cavity of the patient until the next treatment.

In some embodiments, the dialysis machine 102 may be configured to perform hemodialysis ("HD"). During HD, the dialysis machine 102 is configured to use diffusion to remove waste products from a patient's blood. A diffusive gradient occurs across the semi-permeable dialyzer between a patient's blood and an electrolyte solution called dialysate or dialysis fluid to cause diffusion. Hemofiltration ("HF") is an alternative renal replacement therapy that relies on a convective transport of toxins from the patient's blood. HF is accomplished by adding substitution or replacement fluid to the extracorporeal circuit during treatment (typically ten to ninety liters of such fluid). The substitution fluid and the fluid accumulated by the patient in between treatments is ultrafiltered over the course of the HF treatment, providing a convective transport mechanism that is particularly beneficial in removing middle and large molecules (in hemodialysis there is a small amount of waste removed along with the fluid gained between dialysis sessions, however, the solute drag from the removal of that ultrafiltrate is not enough to provide convective clearance).

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

The example dialysis machine 102 may be located in a center, a hospital, or a patient's home. A trend towards home dialysis exists today in part because home dialysis can be performed daily, offering therapeutic benefits over in-center dialysis treatments, which occur typically bi- or tri-weekly. Studies have shown that frequent treatments remove more toxins and waste products than a patient receiving less frequent but perhaps longer treatments. A patient receiving treatments more frequently does not experience as much of a down cycle as does an in-center patient, who has built-up two or three days' worth of toxins prior to treatment. In certain areas, the closest dialysis center can be many miles from the patient's home causing door-to-door treatment time to consume a large portion of the day. Home dialysis may take place overnight or during the day while the patient relaxes, works or is otherwise productive. Much of the appeal of a home treatment for the patient revolves around the lifestyle flexibility provided by allowing the patient to perform treatment in his or her home largely according to his or her own schedule.

Any of the above dialysis modalities performed by the dialysis machine 102 may be run on a scheduled basis and may require a start-up procedure. For example, dialysis patients typically perform treatment on a scheduled basis, such as every other day, daily, etc. Dialysis treatment machines typically require a certain amount of time before treatment for setup, for example, to run a priming and/or disinfection procedure. During a priming procedure, a fluid is pumped through one or more dialysis tubes/lines and/or cassettes to remove air and/or in-line particulates. Priming dialysis tubes/lines and/or cassettes prevents air and/or the particulates from coming into contact with the patient.

The example dialysis machine 102 of FIG. 1 includes a priming sensor 104 configured to detect appropriate priming of at least one dialysis tube/line. In the illustrated embodiment, the priming sensor 104 is configured to detect priming of a patient tube 106. In other embodiments, the priming sensor 104 is configured for priming of additional or alternative tubes, such as to-patient tubes/from-patient tubes of a continuous flow peritoneal dialysis set, drain tubes, heating tubes, source fluid tubes, concentrate tubes, etc. For HD, the priming sensor 104 may be configured to prime an extracorporeal circuit, a to-dialyzer tube, a from-dialyzer tube, a source tube, a blood tube, a saline tube, and/or a drain tube. The patient tube 106 may be made of any suitable medical grade material, such as polyvinyl chloride ("PVC"), silicone, or other non-PVC material. The tube 106 in one embodiment has an inner or outer diameter that is equal to or less than 0.5 inch (12 millimeter).

The dialysis machine 102 in the illustrated embodiment includes at least one pump 110 configured to move fluid from a fluid source 112 to the patient tube 106. The pump 110 may include any type of pump, including a peristaltic pump, a rotary pump, a gear pump, a linear actuator pump, a diaphragm pump, etc. The pump 110 may be operated to prime the patient tube 106 with dialysis fluid. The pump 110 may also be operated to provide dialysis fluid from the fluid source 112 to a patient when the patient tube 106 is connected to a catheter that is inserted into a patient's peritoneal cavity. Priming may alternatively or additionally be performed using gravity where, for example, a source of fluid is provided at head height and permitted to flow through one or more tubes.

In some embodiments, the dialysis machine 102 includes a disposable cassette which is connected fluidly to the tubes. The cassette may include one or more flexible membranes or chambers that operate with valves and/or pumps in the dialysis machine 102. Priming may include moving fluid through the disposable cassette in addition to the one or more tubes.

The fluid source 112 may include one or more containers of pre-mixed dialysis fluid. In some embodiments, the fluid source 112 may include containers or reservoirs of concentrate that have been mixed with pure water to form dialysis fluid. Additionally or alternatively, the fluid source 112 may include an on-line source, such as a source of purified water that is mixed with one or more concentrates to form dialysis fluid. Moreover, in some examples, the fluid source 112 may include a fluid preparation device that provides prepared dialysis fluid to the dialysis machine 102 via one or more fluid connections.

The example dialysis machine 102 of FIG. 1 also includes a processor 120 and a memory 122. The processor 120 may include any type of device capable of processing inputs and performing one or more calculations to determine one or more outputs. The processor 120 may include a microcontroller, a controller, an application specific integrated circuit ("ASIC"), a central processing unit included on one or more integrated circuits, etc. The memory 122 may include any volatile or non-volatile data/instruction storage device. The memory 122 may include, for example, flash memory, random-access memory ("RAM"), read-only memory ("ROM"), Electrically Erasable Programmable Read-Only Memory ("EEPROM"), etc. The example memory 122 is configured to store one or more instructions that are executable by the processor 120 to cause the processor 120 to perform operations disclosed herein. The instructions may be part of one or more software programs or applications. References herein to the processor 120 being configured to perform an operation may include embodiments where the memory 122 stores instructions that are configured to cause the processor 120 to perform the described operation.

The example memory 122 is configured to store instructions that cause the processor 120 to operate the dialysis machine 102. The operations performed by the processor 120 include providing control signals or instructions to the pump 110, which cause the pump 110 to move dialysis fluid from the fluid source 112 to the patient tube 106 during a priming sequence or during a dialysis treatment. The operations performed by the processor 120 also include sending signals and/or messages to the priming sensor 104 to activate one or more light emitters and receive output data from a detector. As disclosed herein, the memory 122 includes instructions that cause the processor 120 analyze the output data to determine a state of the patient tube 106.

The example processor 120 is also configured to transmit one or more messages to a user interface 124 of the dialysis machine 102 for displaying or otherwise conveying information on a display screen, such as a touchscreen. The processor 120 may cause the user interface 124 to display instructions to a patient for preparing the dialysis machine 102 for a treatment, including actions to prepare for a priming sequence. The user interface 124 may also display or otherwise convey indications indicative of alert conditions, such as a warning to place the patient tube 106 within the priming sensor 104 or to connect the patient tube 106 to a catheter after a priming sequence has been completed. The user interface 124 may include a touchscreen overlay and/or electromechanical actuators, buttons, and/or switches to enable an operator to input information. The input may include a prompt from an operator to begin a priming sequence or a dialysis treatment.

It should be appreciated that the dialysis machine 102 may include additional components for therapy preparation and/or performing dialysis therapies. The additional components may include pump actuators, compressors pneumatic equipment, valve actuators, heaters, online fluid generation equipment, fluid pressure sensors, fluid temperature sensors, conductivity sensors, air detection sensors, blood leak detection sensors, filters, dialyzers, balance chambers, sorbent cartridges, etc. In addition, the dialysis machine 102 may include one or more network connections (e.g., an Ethernet connection) to enable the processor 120 to receive data/prescriptions and transmit dialysis therapy status information to a remote or centralized server via a network (e.g., the Internet). In an embodiment, the processor 120 may create a data structure or log that includes an indication of priming, detection of patient tube state changes, a date/time when the state change occurred, and/or indications of alarms provided.

Priming Sensor Embodiment

Figure 2:
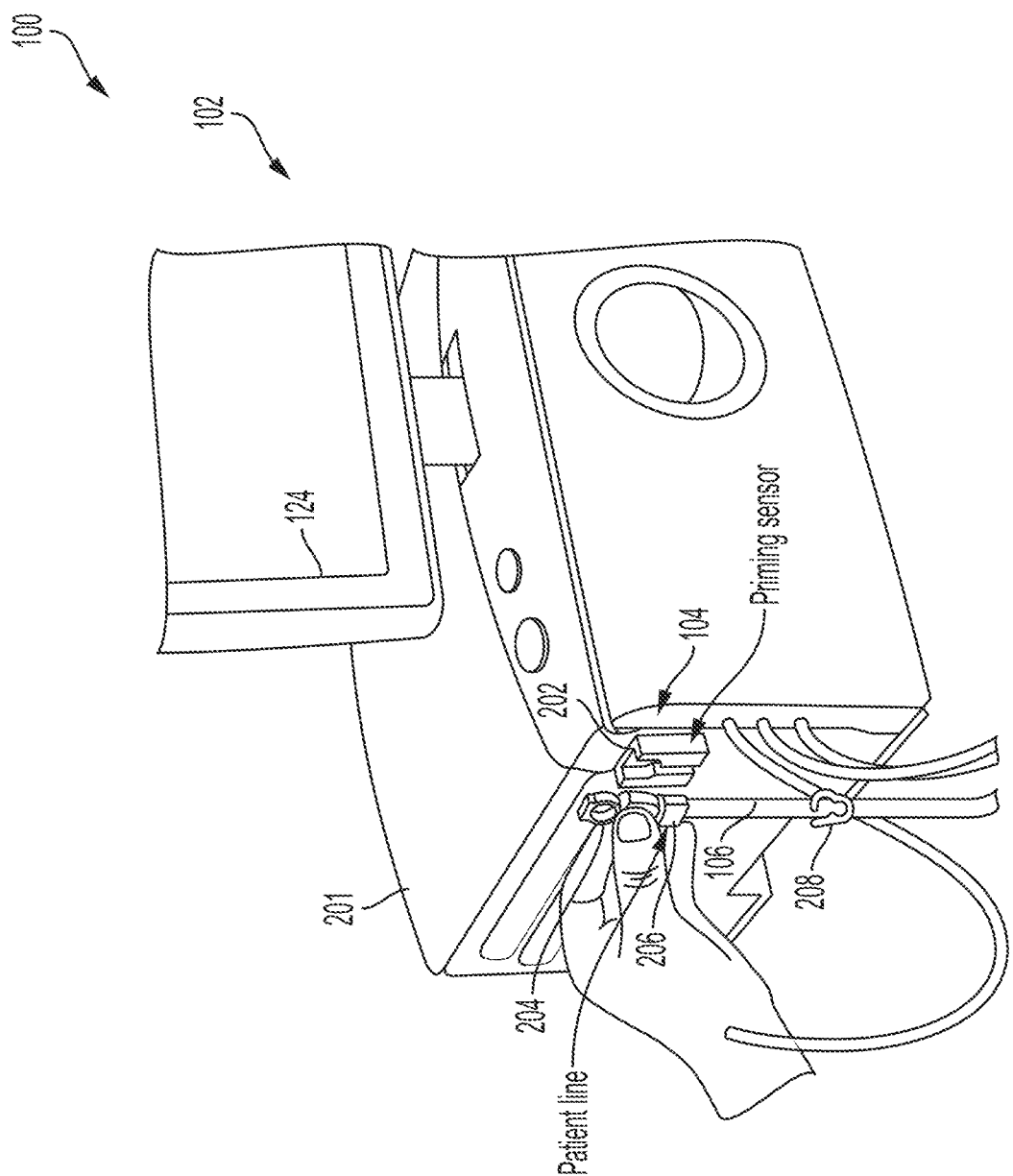
FIG. 2 is a perspective view illustrating a diagram of the priming sensor relative to the dialysis machine of the example medical fluid delivery system of FIG. 1, according to an example embodiment of the present disclosure.

FIG. 2 illustrates a diagram of the priming sensor 104 being positioned relative to the dialysis machine 102 of the example medical fluid delivery system 100 of FIG. 1, according to an example embodiment of the present disclosure. In the illustrated example, the priming sensor 104 is provided on a housing 201 of the dialysis machine 102. The priming sensor 104 includes a holder section 202 that is configured to retain the patient tube 106 in place to enable measurements to be made. The holder section 202 may include a clip configured to engage with a cap 204 attached to the patient tube 106. For example, the holder section 202 may include an aperture that corresponds to or aligns with dimensions of a cap 204 to retain the cap 204 in place. A patient couples the cap 204 to the holder section 202 by placing the patient tube 106 into an open channel of the holder section 202. The patient then lowers the cap 204 until it is seated within the holder section 202. While the holder section 202 is shown as being on a side of the dialysis machine 102, in other embodiments, the holder section may be on a top, front, back, and/or opposing side of the dialysis machine.

The example cap 204 is configured to mechanically connect to an end connector 206 of the patient tube 106. The cap 204 may include a hydrophobic vent or filter that permits air to vent from the patient tube 106 during a priming sequence. The vent or filter, in an embodiment, prevents fluid from overflowing out of the patient tube 106. The priming sensor 104 is configured to detect when fluid reaches the end connector 206 (or just below the connector 206) of the patient tube 106 to determine when fluid pumping or gravity priming should stop. After a priming sequence has been completed, a patient may disconnect the cap 204 from the end connector 206. The patient may then connect the end connector 206 of the patient tube 106 to a catheter, which is fluidly connected to the patient's peritoneal cavity.

FIG. 2 also illustrates that the patient tube 106 may include a tube clamp 208. The tube clamp 208 may be clamped to the tube 106 prior to priming to prevent fluid from unintentionally exiting the patient tube 106. The tube clamp is disengaged prior to the priming sequence, but may be clamped after priming while the patient connects the end connector 206 to a catheter (or related transfer set) to begin treatment. In some embodiments, the tube clamp 208 may be omitted.

Figure 3:
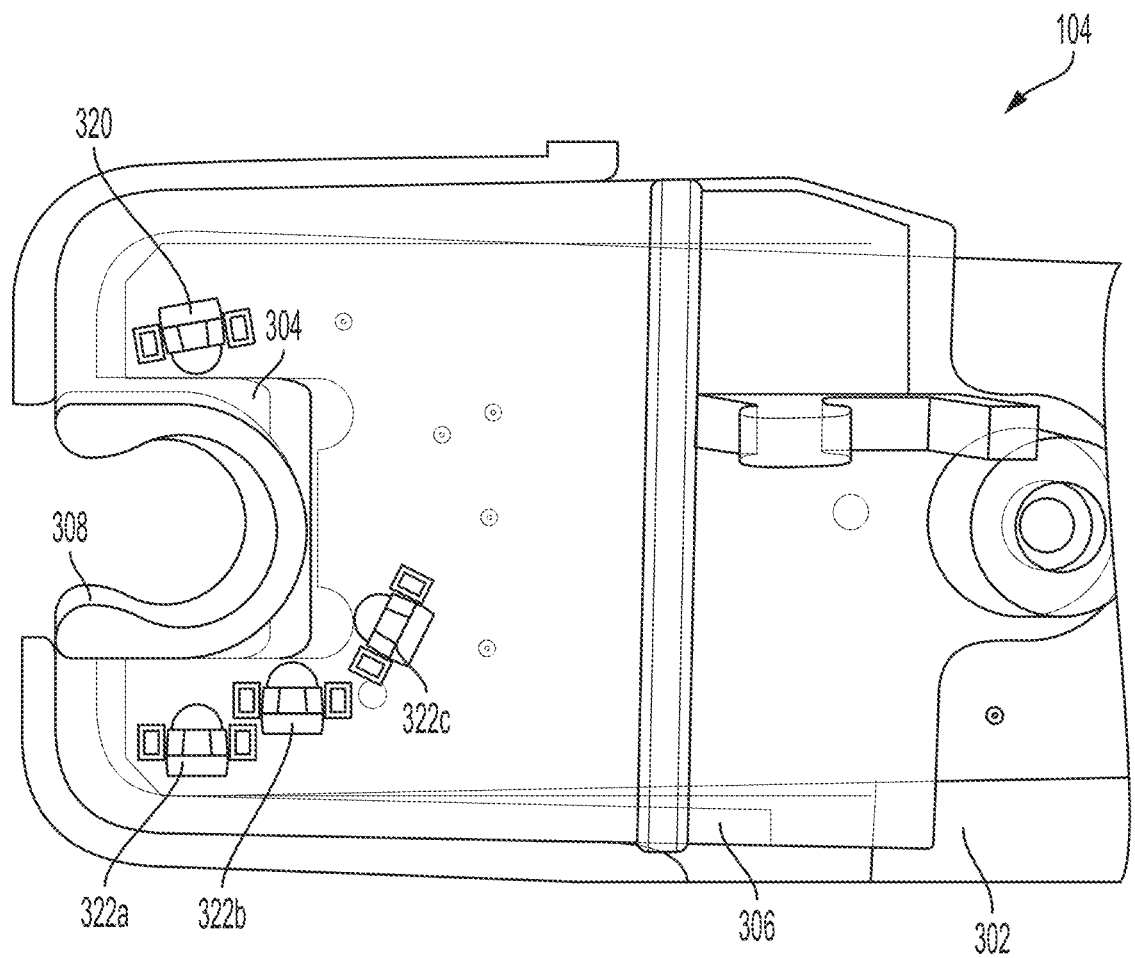
FIGS. 3 and 4 are top-plan views showing a circuit board of the priming sensor of FIGS. 1 and 2, according to an example embodiment of the present disclosure.

FIG. 3 illustrates a diagram of a circuit board 302 of the priming sensor 104 of FIGS. 1 and 2, according to an example embodiment of the present disclosure. In the illustrated example, the circuit board 302 includes a cutout or aperture 304 to receive at least a portion of the patient tube 106 and/or the end connector 206. The aperture 304, in the illustrated embodiment, has a U-shape. In other embodiments, the aperture 304 may have a circular or oval-shape. A cover 306 is provided at the aperture-end of the circuit board 302 and may extend to cover the entire circuit board.

The example cover 306 is transparent or near-transparent and is configured to protect the circuit board 302 from spilled or dripped dialysis fluid. In the illustrated embodiment, the cover 306 may be made of any plastic or glass material. The cover 306, in the illustrated embodiment, includes a retainer section 308, which has a circular shape. The retainer section 308 is aligned with the aperture 304 and is configured to accept, retain, or otherwise hold the patient tube 106 and/or the end connector 206 within the priming sensor 104.

FIG. 3 illustrates that the priming sensor 104, in an embodiment, includes a detector 320 and three emitters 322. In other examples, the priming sensor 104 may include additional detectors 320 and emitters 322. In the illustrated example, the detector 320 is located on a side of the circuit board that is opposite from the three emitters 322. Light emitted from the emitters passes across the aperture 304 to reach the detector 320, thereby enabling tube measurements to be performed when the patient tube 106 is placed within the retainer section 308.

Figure 4:
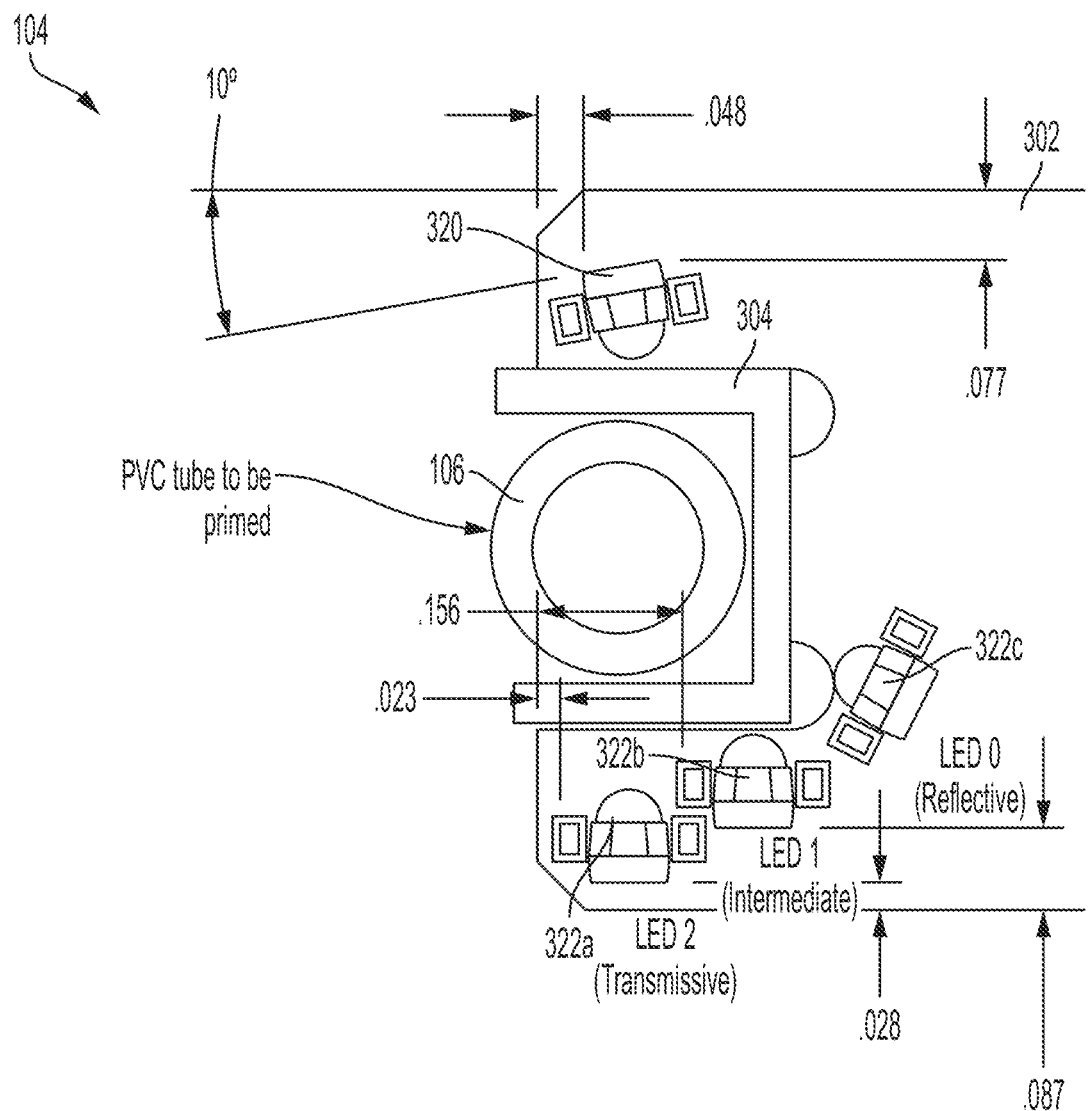

FIG. 4 illustrates a diagram of one possible positioning of the detector 320 relative to the emitters 322 on the circuit board 302. In an example, a first emitter 322a is positioned to be on an opposite side of the detector 320 and positioned to emit light directly towards the detector 320 at approximately a 0° angle. In addition, the second emitter 322b is positioned on the circuit board 302 adjacent to the first emitter 322a and is configured to emit light at the same approximate 0° angle as the first emitter 322a. The third emitter 322c is positioned adjacent to the second emitter 322b on the circuit board but is positioned at an angle between 20° and 70° relative to light emitted from the first emitter 322a and the second emitter 322b. It should be appreciated that in other examples, the emitters 322 may be positioned to direct light at different angles towards the detector 320.

The example detector 320 is positioned at an approximate angle of 10° offset from pointing directly at the first emitter 322a. In other examples, the 10° offset may be larger or smaller. The positioning of the detector 320 relative to the emitters 322 enables the detector 320 to receive transmissive light from the first emitter 322a, intermediate/partially reflective light and partially transmissive light from the second emitter 322b, and reflective light from the third emitter 322c. Reception of transmissive and reflective light during a sweep pattern helps enable the processor 120 to create waveforms with unique and differential patterns between different tube states.

The dimensions shown in FIG. 4 are provided in inches for illustrative purposes only and are exemplary of possible dimensions for positioning the emitters 322 relative to the detector 320 and the patient tube 106. In other embodiments, the dimensions may be represented in centimeters. Alternatively, the dimensions of the priming sensor 104 may be greater and/or smaller.

The example detector 320 of FIGS. 3 and 4 may include any type of light detector, such as a phototransistor. The detector 320 is configured to provide a digital or analog output that is indicative of a brightness of detected light. In some instances, the detector 320 may transmit output data at a sample rate and/or upon request by the processor 120. Alternatively, the detector 320 may continuously transmit output data that is indicative of detected light brightness, in which the processor 120 samples the received data.

The example emitters 322 of FIGS. 3 and 4 may include any type of light emitter, such as infrared light emitting diodes ("LEDs"). The emitters 322 may be powered by receiving, for example, five-volt DC power via a power supply component of the dialysis machine 102 or via the processor 120. A brightness of the emitters 322 is controlled, in an embodiment, via a filtered pulse-width modulated ("PWM") signal provided by the processor 120. A duty-cycle of the PWM signal is controlled by the processor 120 for adjusting the brightness of the light that is emitted by the emitters 322. In some instances, the processor 120 may ramp the duty cycle from 0% to 100% over a time period to cause any one or more of the emitters 322 to transition from being off to full or peak brightness.

Figure 5:
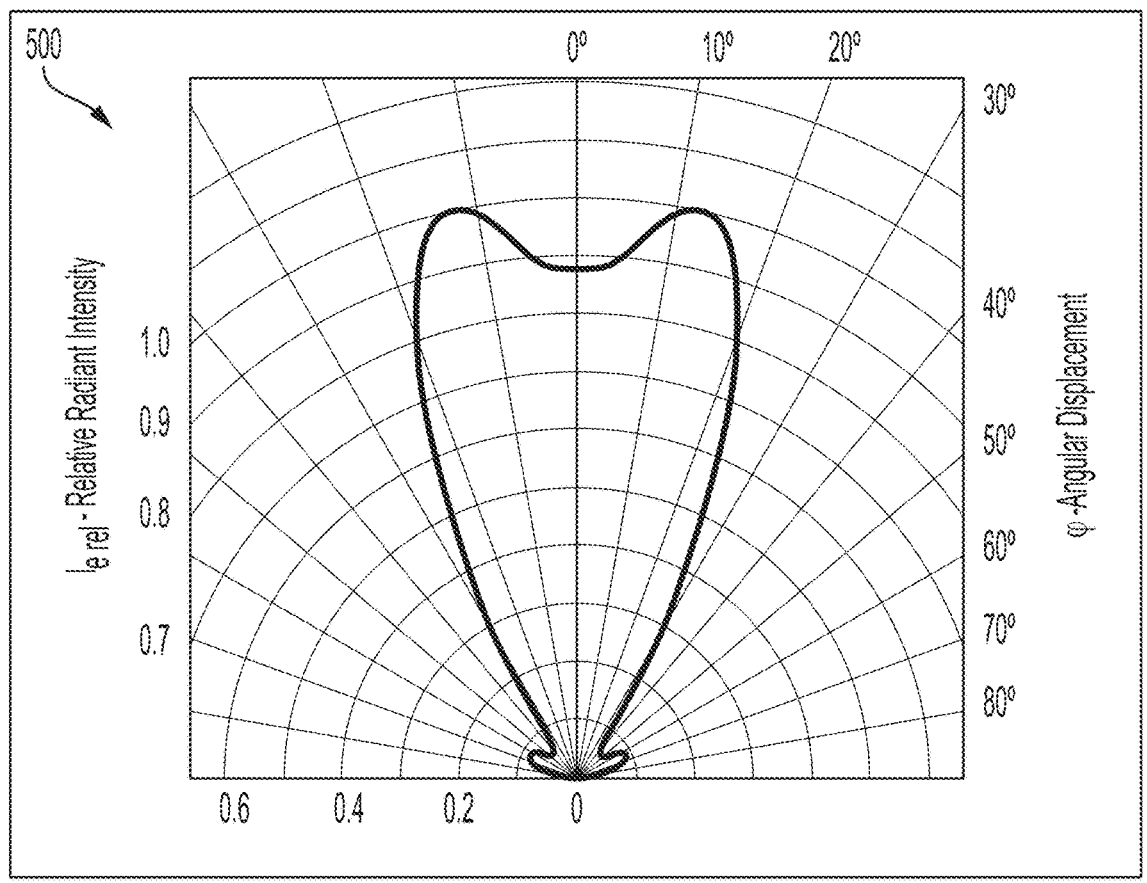
FIG. 5 is a diagram of a directional radiation pattern for emitters of the priming sensor of FIGS. 3 and 4, according to an example embodiment of the present disclosure.

FIG. 5 illustrates a diagram of a directional radiation pattern 500 for the emitters 322 of FIGS. 3 and 4, according to an example embodiment of the present disclosure. The pattern 500 shows that light intensity, in the present example, is greatest between +/−10° to 15° from direct emission (at 0°). The emitted light decreases in intensity significantly between +/−20° to 30° from direct emission, which enables precise light directivity control. In other examples, different emitters 500 may produce different radiation patterns.

Figure 6:
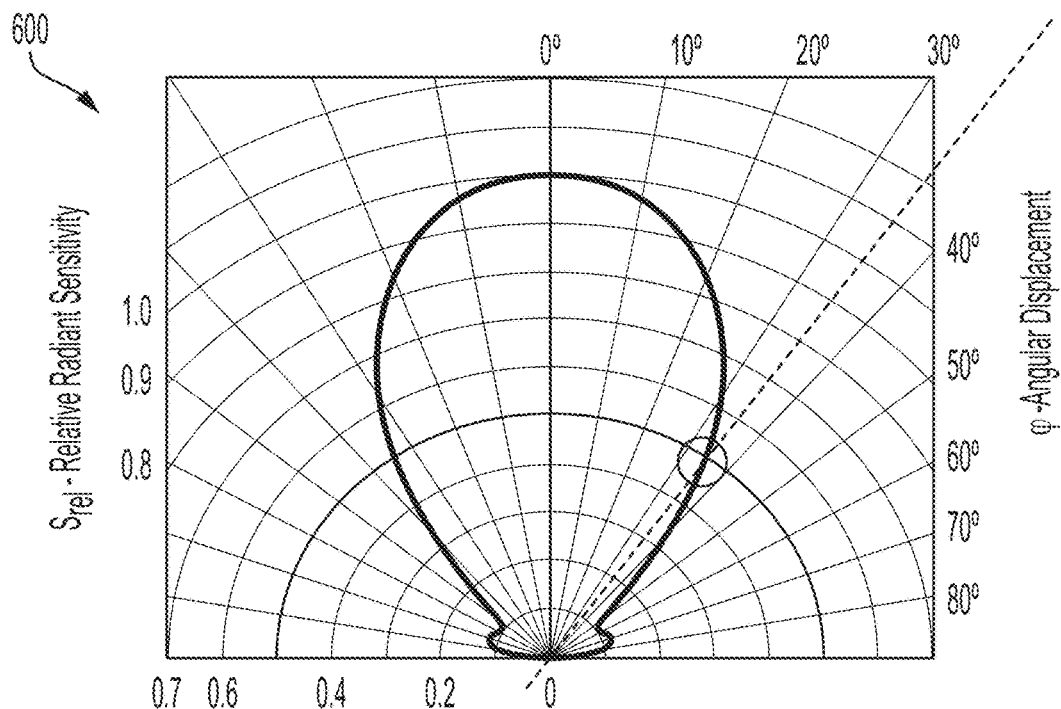
FIG. 6 is a diagram of a directional radiation sensitivity pattern of a detector of the priming sensor of FIGS. 3 and 4, according to an example embodiment of the present disclosure.

FIG. 6 illustrates a diagram of a directional radiation sensitivity pattern 600 of the detector 320 of FIGS. 3 and 4, according to an example embodiment of the present disclosure. In the illustrated example, the detector 320 is most sensitive between an angular displacement of +/−5°. The sensitivity of the detector 320 decreases significantly after an angular displacement of +/−20°.

The patterns 500 and 600 of FIGS. 5 and 6 illustrate that any angular displacement greater than +/−5° between the detector 320 and the emitters 322 results in detected light brightness being less than the brightness emitted, as measured at the peak intensity. In addition the steep drop off in the patterns 500 and 600 enables significantly different waveforms to be formed based on the different states of the patient tube 106 since the tube, and any fluid contents, cause at least a portion of the emitted light to reflect/refract.

Processor Embodiment

The example processor 120 of FIG. 1 is configured, in part, to determine a waveform for detecting a state of a patient tube. FIG. 7A shows a diagram that illustrates how the processor 120 operates with the priming sensor 104 for forming a sweep pattern 700 and detecting emitted light, according to an example embodiment of the present disclosure. The processor 120 is configured to operate the sweep pattern periodically to determine a tube state. For example, the processor 120 may operate the sweep pattern 700 every millisecond, 100 milliseconds, 500 milliseconds, 1000 milliseconds, 2500 milliseconds, etc. It should be appreciated that in other examples, the processor 120 may be configured to apply different sweep patterns than the pattern 700 shown in FIG. 7A. For example, the processor 120 may not activate a subsequent emitter 322 until after a first emitter 322 is deactivated or turned off.

The example processor 120 is configured to transmit one or more messages or control an analog signal provided to each of the emitters 322 in a controlled manner so as to create the sweep pattern 700. The messages may specify, for example, a duty cycle percentage. Alternatively, an analog signal to control brightness may be set by the processor 120 according to the desired duty cycle. Instructions stored in the memory 122 may define how the duty cycle changes over a time period for each of the emitters 322 to create the sweep pattern 700.

Figure 7B:
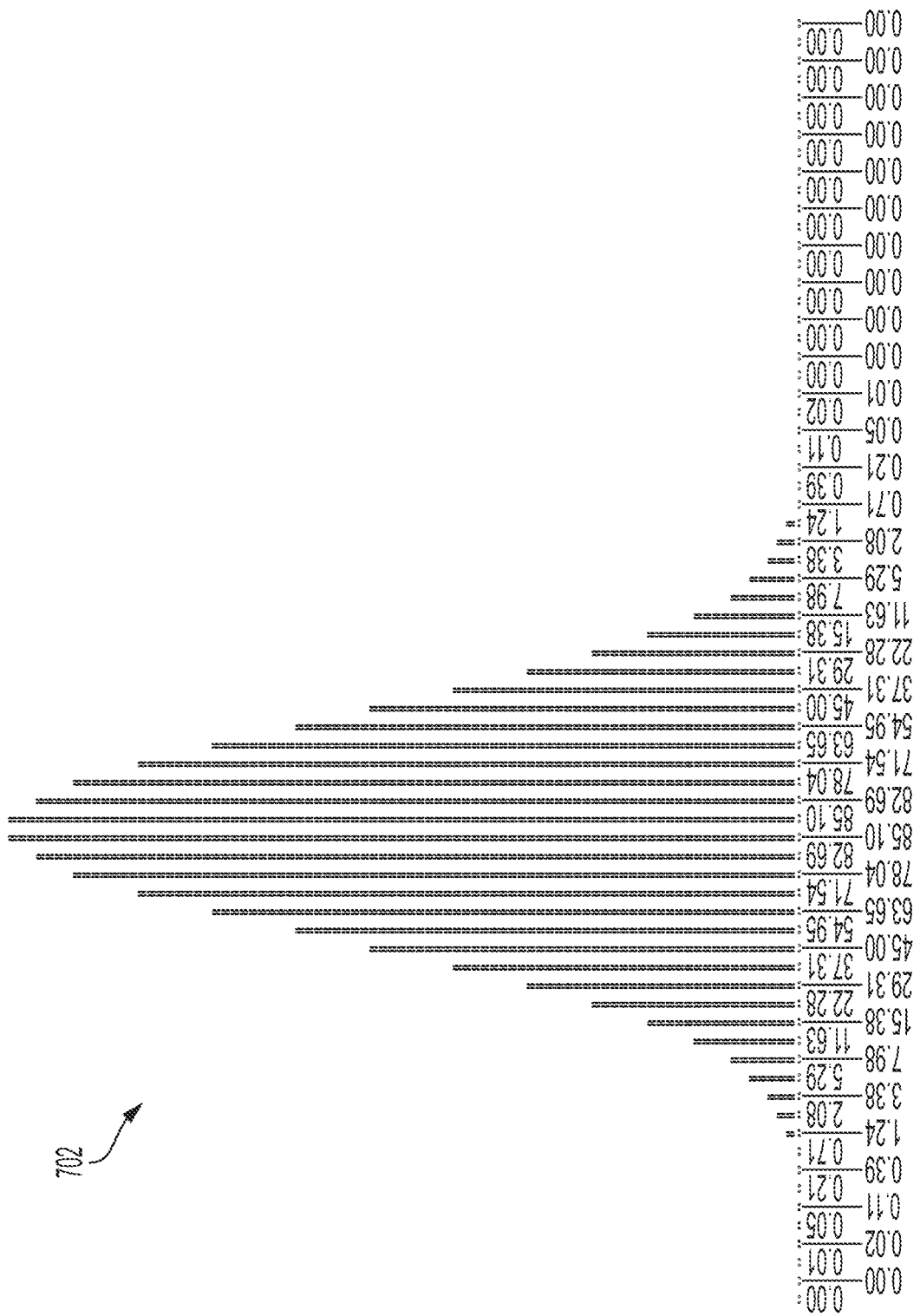

In the illustrated example, the processor 120 causes the emitter 322a to emit a first impulse pattern 702 during a first time period 704, which is a first component of the aggregate sweep pattern 700. The impulse pattern 702 begins with the emitter 322 being set at a relatively low duty cycle, such as 0% or 5%. At a mid-point of the time period 704, the duty cycle is relatively high (e.g., 75% to 100%), which increases the intensity of light brightness. For the remainder of the time period 704, the processor 120 is configured to decrease the duty cycle causing the emitter 322a to reduce the brightness of light emitted. FIG. 7B shows another embodiment of the impulse pattern 702, which has a non-Gaussian shape. The values along the x-axis represent a power level (over the first time period 704) provided to the emitter 322a, which is proportional to a duty cycle for emitted light brightness.

Figure 7C:
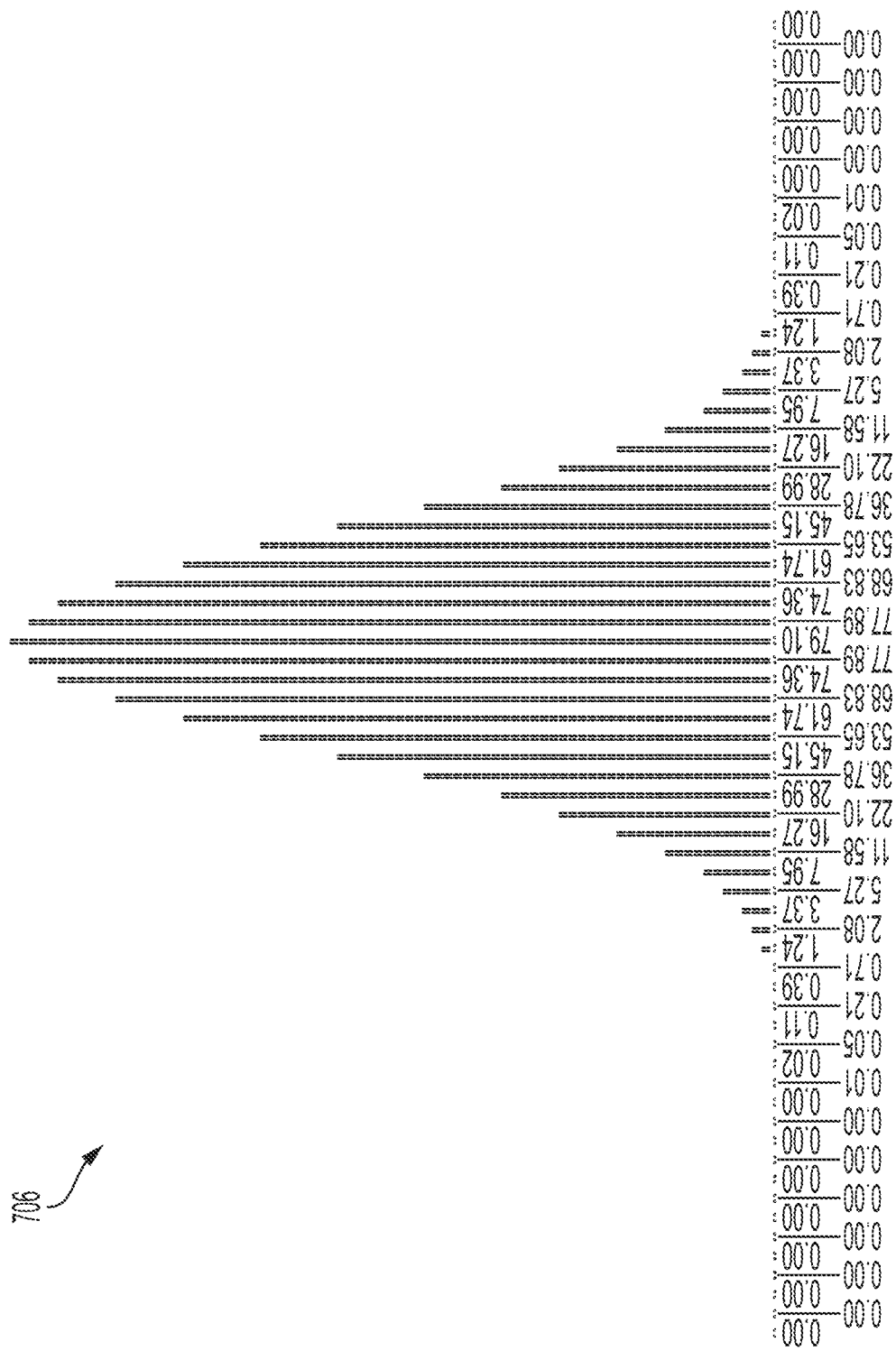

Returning to FIG. 7A, during a second time period 708, the processor 120 causes the emitter 322b to emit a second impulse pattern 706. As illustrated, the second time period 708 begins at a mid-point of the first time period 704. In other examples, the second time period 708 may begin ¼, ⅓, ⅔, ¾, ⅞, or at other times through the first time period 704. Alternatively, the second time period 708 may begin after or just as the first time period 704 has ended. The impulse pattern 706 may be same as the impulse pattern 702, or may have a different shape. FIG. 7C shows another embodiment of the impulse pattern 706, which has a non-Gaussian shape.

Figure 7D:
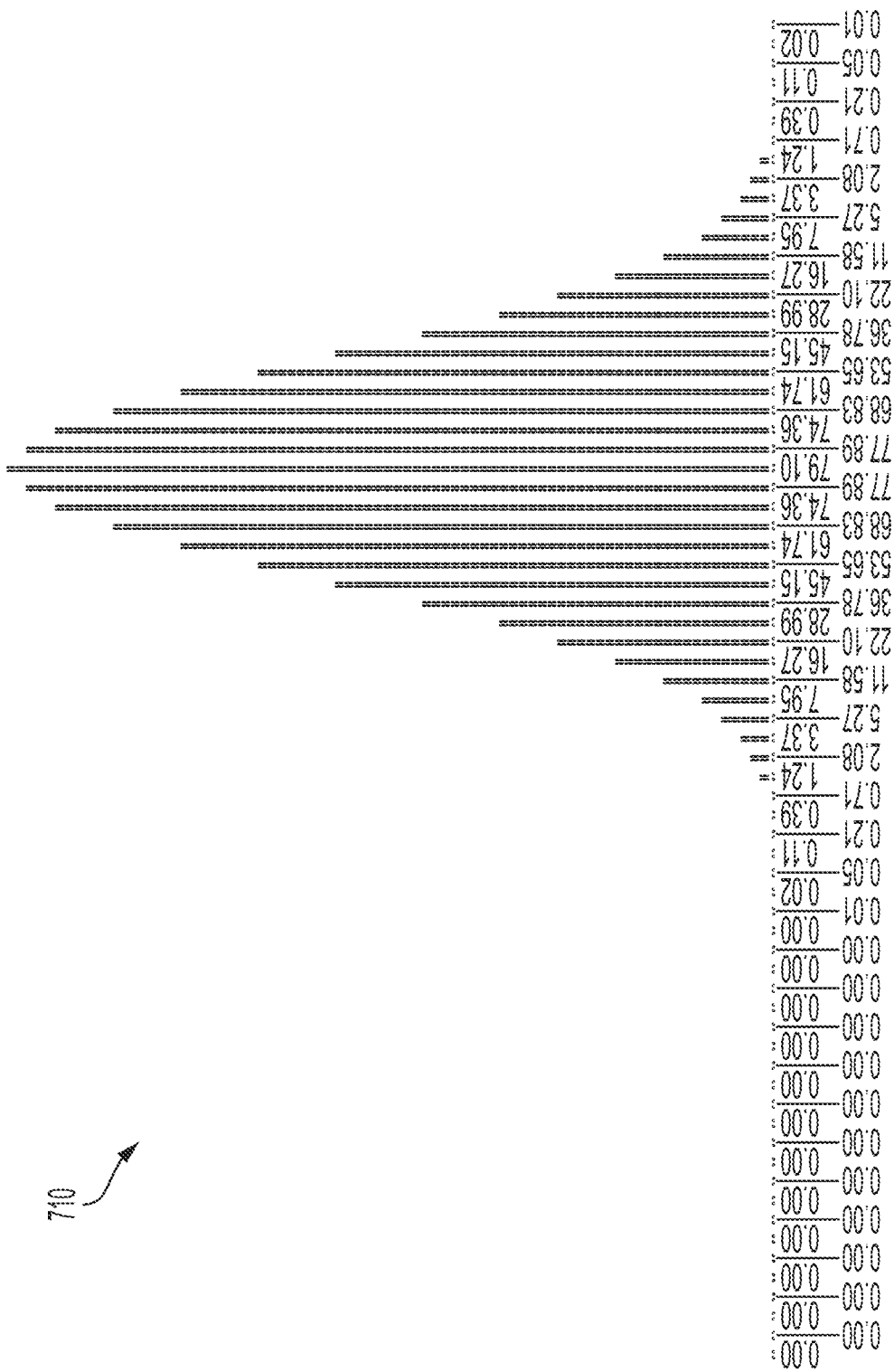

During a third time period 712, the processor 120 causes the emitter 322c to emit a third impulse pattern 710. As illustrated, the third time period 712 begins at a mid-point of the second time period 708. In other examples, the third time period 712 may begin ¼, ⅓, ⅔, ¾, ⅞, or at other times through the second time period 708. Alternatively, the third time period 712 may begin after or just as the second time period 708 has ended. The impulse pattern 710 may be same as the impulse patterns 702 and 706, or may have a different shape. FIG. 7D shows another embodiment of the impulse pattern 710, which has a non-Gaussian shape.

Figure 7E:
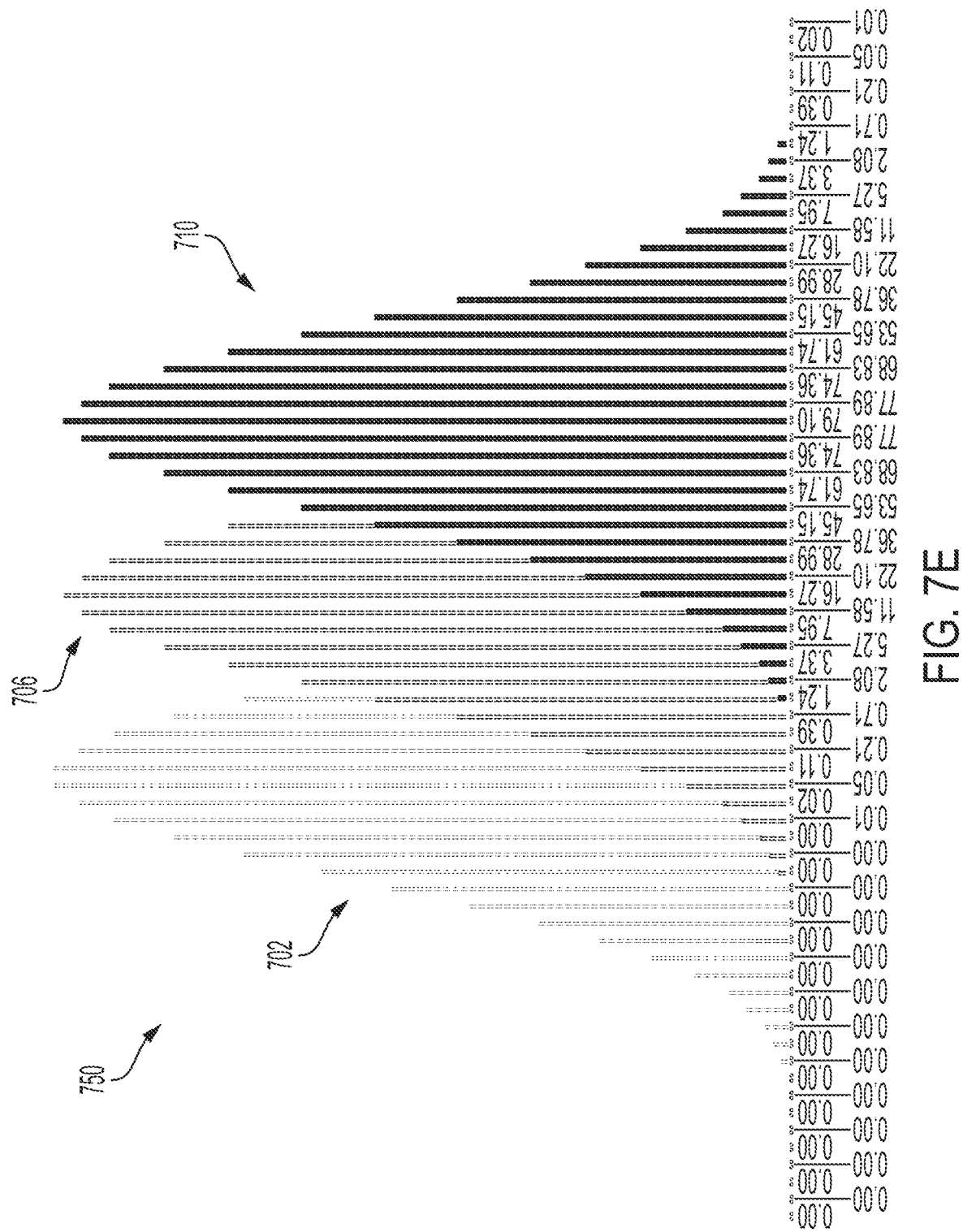

FIG. 7E shows a diagram of a composite waveform 750 of the impulse patterns 702, 706, and 710 overtime. As shown, the patterns 702, 706, and 710 have slight differences in slope and width between them. In addition, the patterns 702, 706, and 710 substantially overlap. In some embodiments, the overlap in the patterns 702, 706, and 710 may correspond to the spacing of the emitters 322 shown in FIGS. 3 and 4. Together, the impulse patterns 702, 706, and 710, collectively shown as the composite waveform 750, form the overall sweep pattern 700 that occurs over a sweep period.

The impulse patterns 702, 706, and 710 are shown as having a bell-curve shape. In other examples, the impulse patterns 702, 706, and 710 may have different shapes corresponding to changes in duty cycle, such as a square-wave shape, a bi-modal shape, a saw-tooth shape, etc. Further, while the impulse patterns 702, 706, and 710 are shown as having the same shape, in other examples, each of the patterns 702, 706, and 710 may be different.

Returning to FIG. 7A, during the sweep pattern 700, the example processor 120 is configured to collect or receive output data samples 720 from the detector 320. In the illustrated example, the height of the lines representative of the data samples 720 are not indicative of light brightness. Rather, the lines for the data samples 720 provide indications of when the light brightness is sampled by the detector 320 and/or the processor 120 relative to the sweep pattern 700. The sampled output data 720 (whether in digital or analog form) provides an indication of an intensity of light sensed by at least one phototransistor of the detector 320. The sampled output data 720 may be transmitted as an analog voltage that is proportional to detected light intensity, or a digital message that is indicative of the light intensity. In some examples, the detector 320 is configured to sample the phototransistor and transmit the output data at the sampled times. In other examples, the detector 320 may continuously monitor detected light. In these other examples, the detector 320 transmits a message or analog signal indicative of the measured light intensity upon receipt of a sampling message/signal from the processor 120 or provides a stream of output data. In the instance of a stream of output data, the processor 120 samples and processes the output data. In an example, the processor 120 and/or detector 320 is/are configured to acquire 10 to 100 samples during the sweep pattern 700, preferably between 50 and 80 samples.

Figure 8:
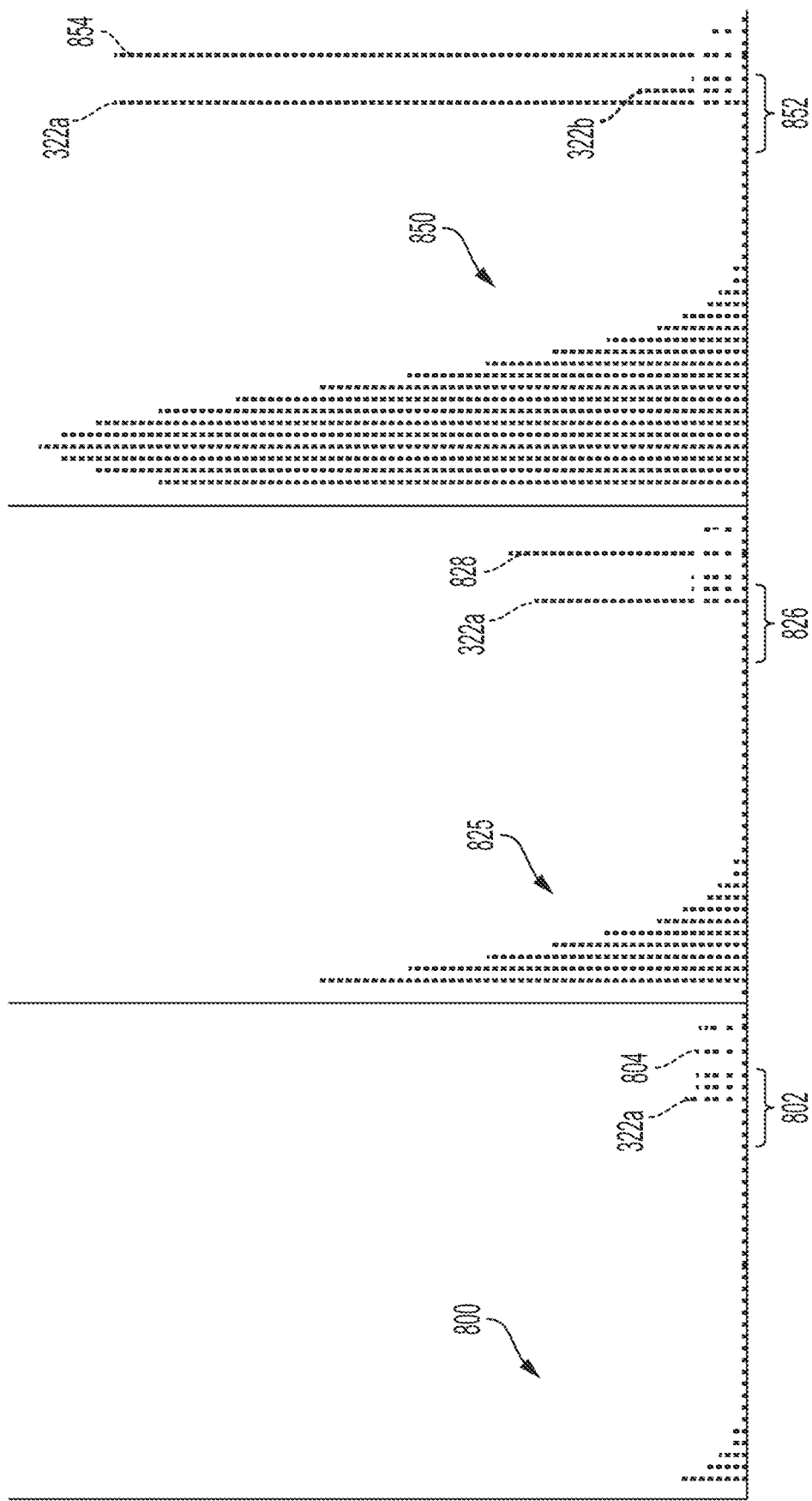
FIGS. 8 and 9 are example graphs that illustrate subsets or portions of the sweep pattern of FIG. 7A for a no-tube state, according to example embodiments of the present disclosure.
Figure 9:
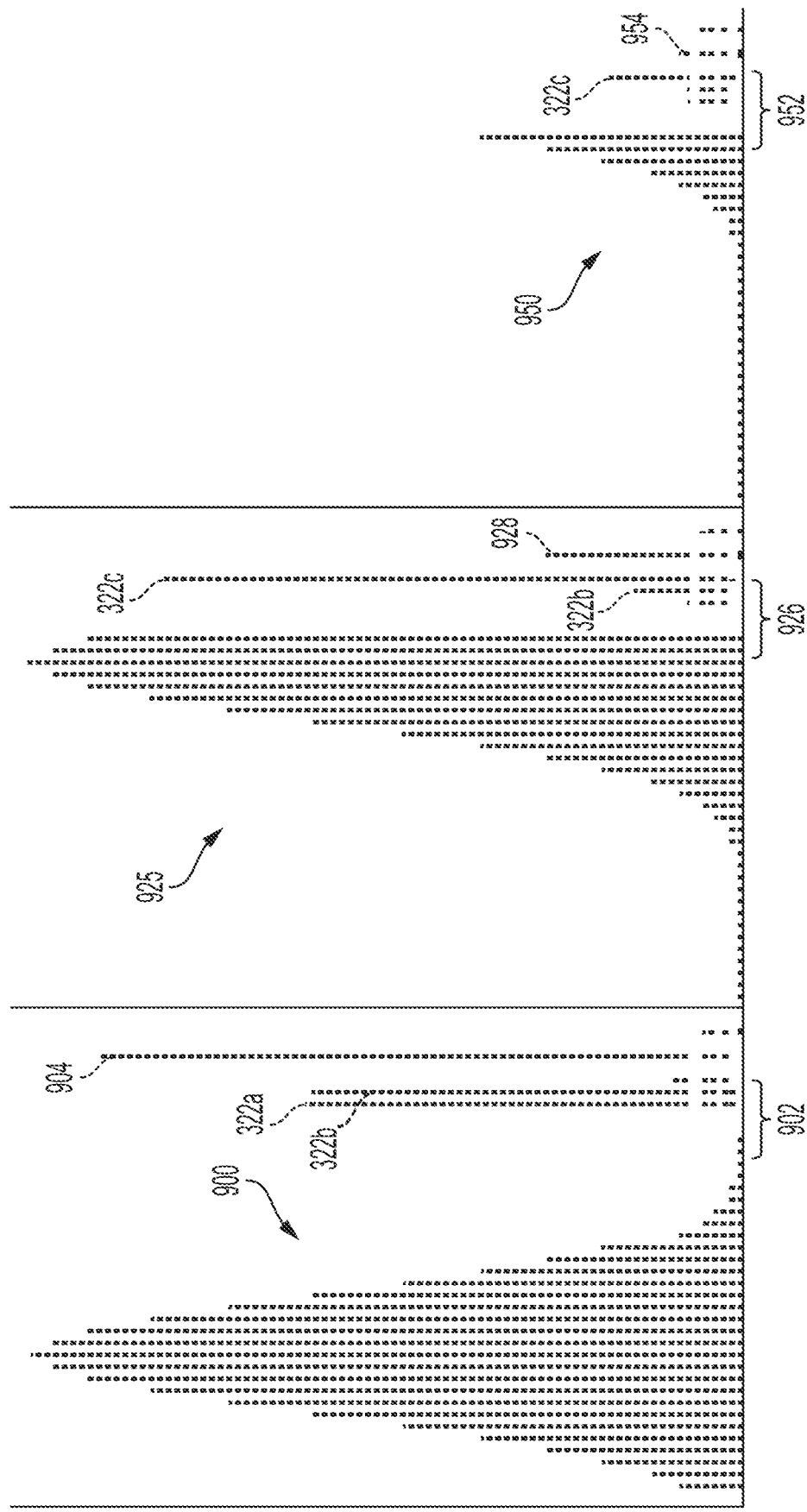

FIGS. 8 and 9 show example graphs 800, 825, 850, 900, 925, and 950 that illustrate subsets or portions of the sweep pattern 700 for a no-tube state, according to example embodiments of the present disclosure. Indexes 802, 826, and 852 illustrate light intensity emitted by each of the emitters at a given point in time during for the respective subset graph 800, 825, and 850, with the left-most bar corresponding to the first emitter 322*a*, the middle bar corresponding to the second emitter 322*b*, and the right-most bar corresponding to the third emitter 322*c*. Bars 804, 828, and 854 are indicative of light intensity that is sensed by the detector 320 at the respective instance of time during the subset graph 800.

The example graph 800 shows that at the start of the sweep pattern 700, only the first emitter 322*a* emits light at a relatively low intensity. The example subset graph 825 shows that over a subsequent time, the intensity of the first emitter 322*a* increases while the other two emitters 322*b* and 322*c* remain off. The example subset graph 850 shows that during another later time, the intensity of detected light is greater as the first emitter 322*a* emits relatively bright light (set by a high duty cycle) with the second emitter 322*b* contributing at least some light.

The graph 900 shows the sweep progress from the first emitter 322*a* to the second emitter 322*b* as both emitters emit light at relatively the same intensity. The graph 925 shows the sweep pattern 700 when the third emitter 322*c* emits the brightest light while the first emitter 322*a* is turned off and the second emitter 322*c* is dimmed. At this point in the sweep pattern 700, the weight of the light intensity has shifted to a point between the second emitter 322*b* and the third emitter 322*c*, shown by the shift in the waveform towards the right. The graph 950 shows an end of the sweep pattern 700 with the first emitter 322*a* and the second emitter 322*b* turned off and a brightness of the third emitter 322*c* being decreased.

Figure 10:
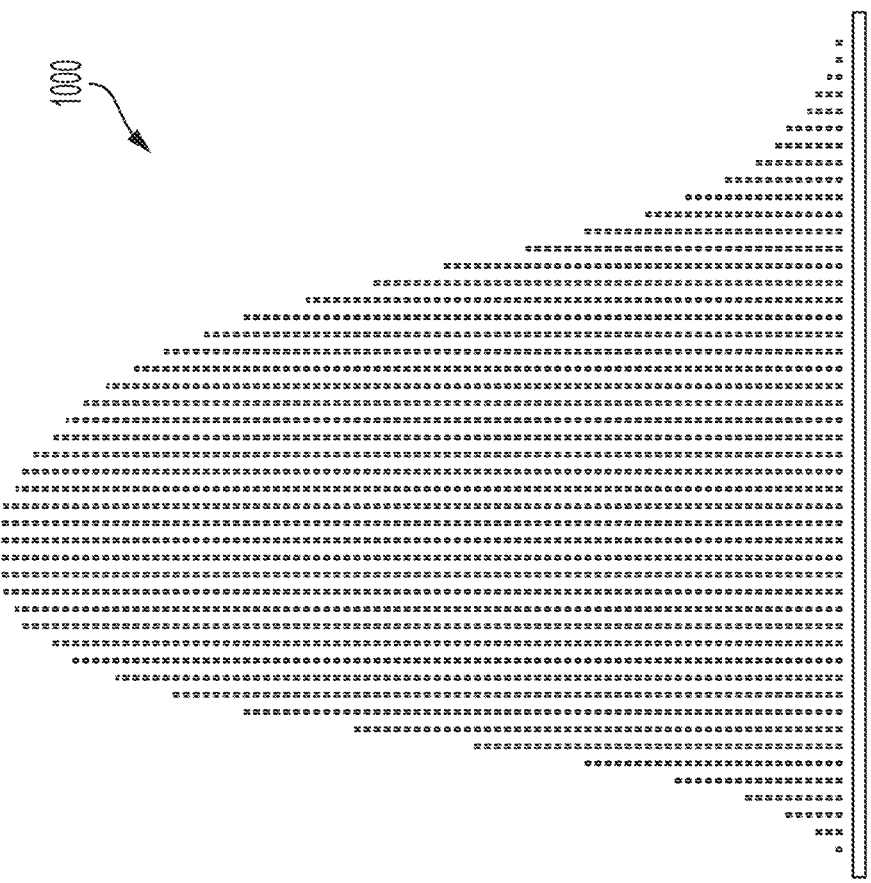
FIG. 10 is a diagram of a waveform formed by aggregating or otherwise combining sampled output data during the sweep period of FIG. 7A for a no-tube state, according to an example embodiment of the present disclosure.

FIG. 10 shows a diagram of a waveform 1000 formed by aggregating or otherwise combining the sampled output data during the sweep period 700 for a no-tube state, according to an example embodiment of the present disclosure. The waveform 1000 is representative of light brightness sensed by the detector 320 during the sweep pattern 700. The example waveform 1000 has a bell-shape as a result of the overlapping impulse patterns (discussed above in connection with FIG. 7A) of the emitters 322. It should be appreciated that the waveform 1000 may change based on the spacing and shape of the impulse patterns selected.

The example processor 120 is configured to compile sampled output data to create a waveform, such as the waveform shown in FIG. 10. The processor 120 may be configured to compare the compiled waveform to one or more reference waveforms to determine a state of the patient tube 106. For example, the processor 120 is configured to determine differences between the waveform and reference waveforms. The differences may include a comparison of peak brightness detected at different points along a sweep period. The processor 120 determines which of the reference waveforms have a smallest difference with a measured waveform. The processor 120 then determines the state of the patient tube 106 based on the selected reference waveform having the smallest difference. In other examples, the processor 120 is configured to perform template matching of the reference waveforms to the acquired waveform to determine a best fit for identifying a state of the tube 106.

In some examples, the processor 120 may remove a common mode offset and accordingly re-scale the acquired waveform to remove effects from ambient light. Additionally or alternatively, the processor 120 may be configured to compute a first derivative of the waveform to determine areas in which a slope of the waveform changes. FIGS. 11 to 16 show graphs of acquired waveforms and correspondingly calculated derivative waveforms (e.g., analytical output waveforms) for different tube states, according to example embodiments of the present disclosure.

Figure 11:
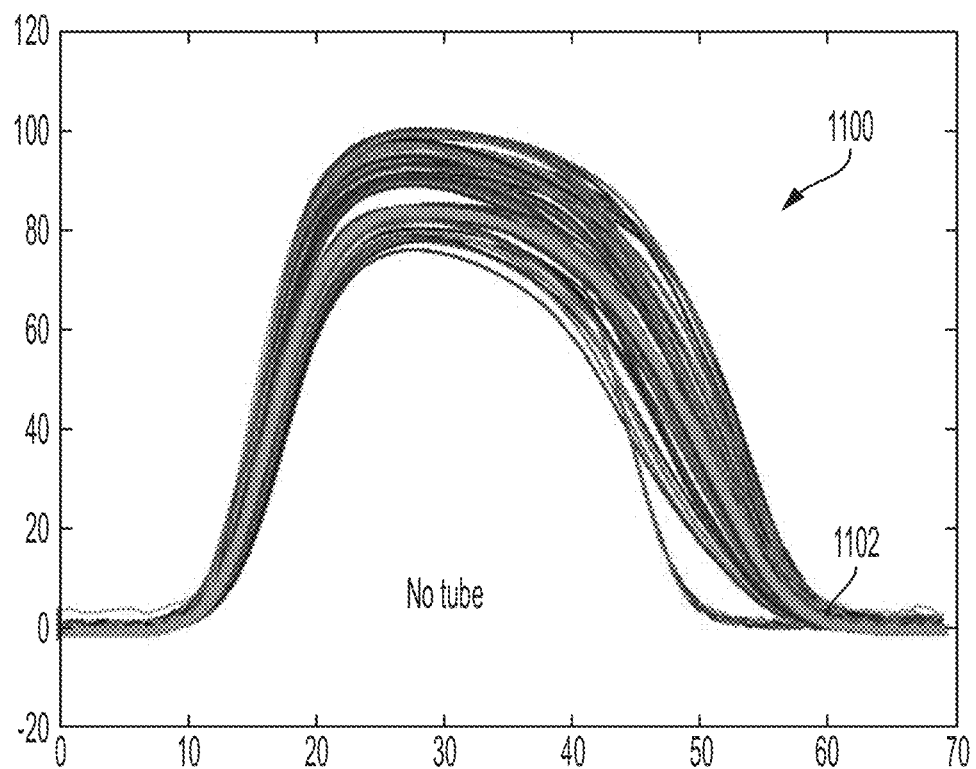
FIGS. 11 to 16 are graphs of acquired waveforms and correspondingly calculated derivative waveforms for different tube states, according to example embodiments of the present disclosure.
Figure 12:
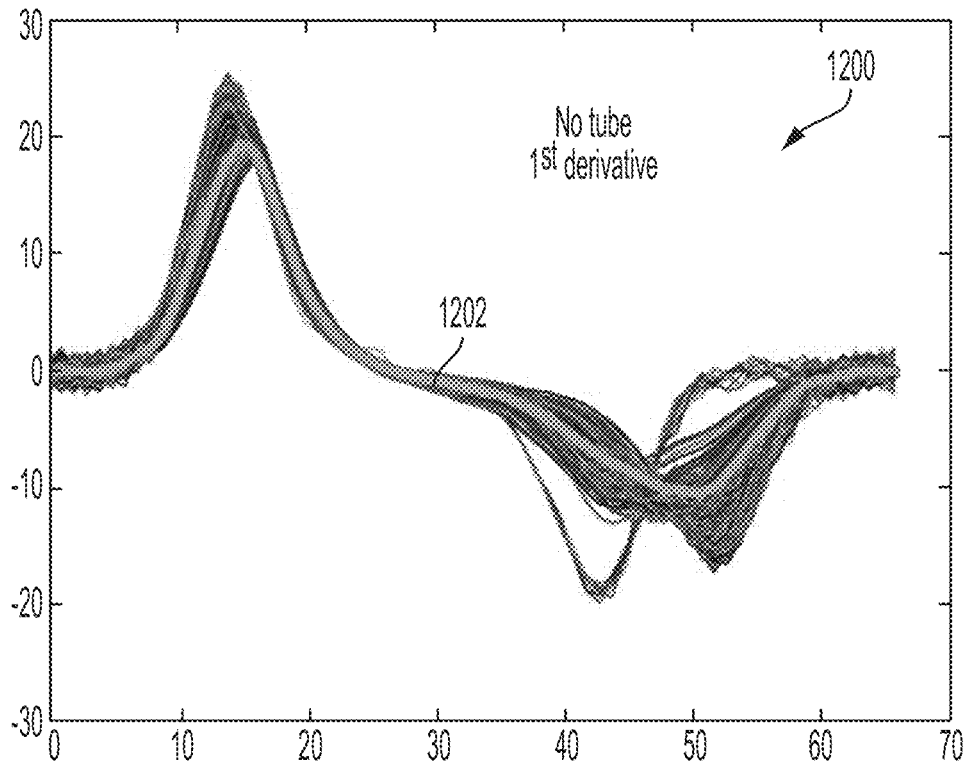

FIG. 11 shows a diagram of acquired waveforms 1100 corresponding to a no-tube state. The acquired waveforms 1100 include about 500 individual waveforms from 500 different sweeps on a large population of priming sensors 104. Similar to the waveform 1000 of FIG. 10, the waveforms 1100 have an approximate bell-shape. Line 1102 (e.g., the thickest line) represents an average of the waveforms 1100 and may be used as a reference waveform for the no-tube state. FIG. 12 shows waveforms 1200, which the processor 120 calculates by determining a first derivative of the waveforms 1100. Line 1202 represents an average of the waveforms 1200 and may additionally or alternatively be used as a reference waveform for the no-tube state. As illustrated, calculation of the first derivative may reduce the variability in the data and provide more consistent waveform sections where a slope of the waveforms 1100 change with respect to the sweep pattern.

Figure 13:
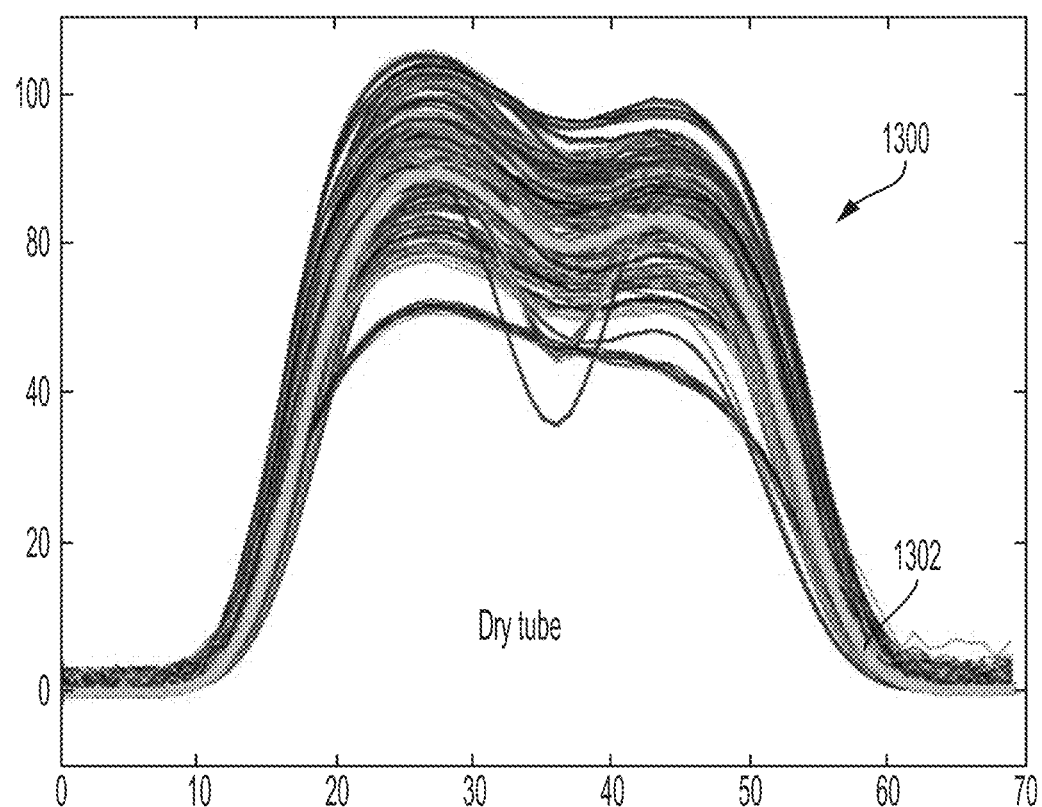
Figure 14:
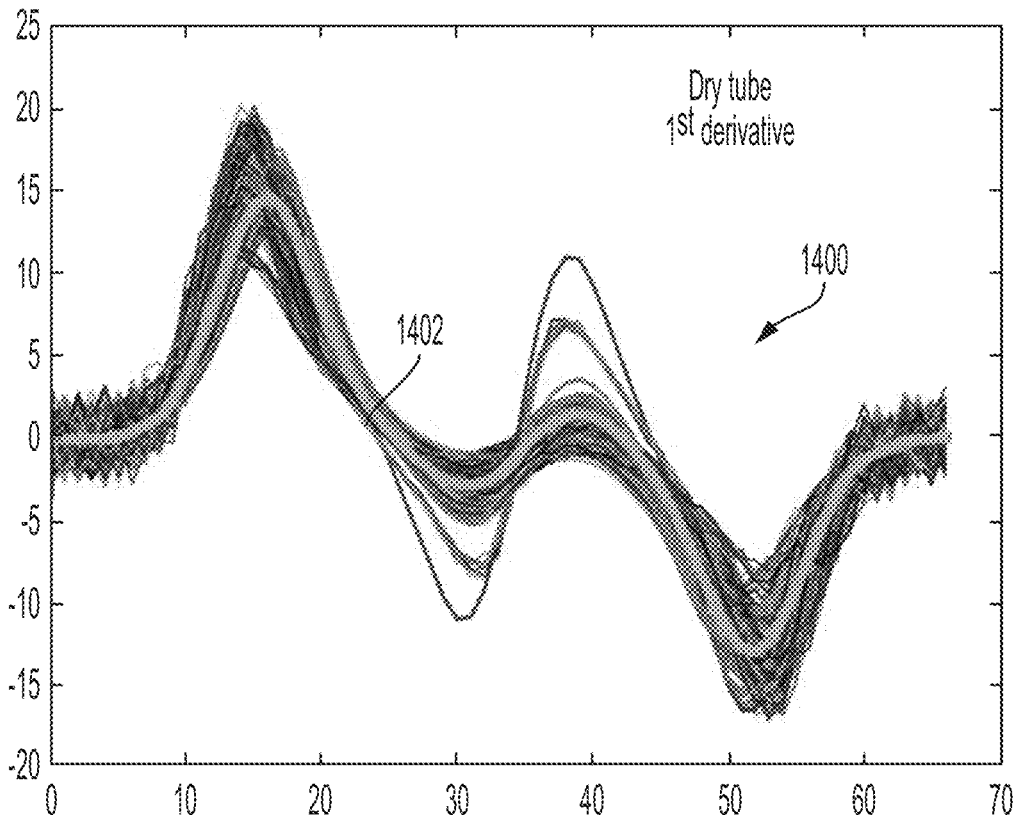

FIG. 13 illustrates a diagram of acquired waveforms 1300 corresponding to a dry tube state. Similar to FIG. 11, the acquired waveforms 1300 include about 500 individual waveforms from 500 different sweeps. Line 1302 represents an average of the waveforms 1300 and may be used as a reference waveform for the dry tube state. The waveforms 1300 show a consistent bell-shaped pattern with an indentation in the middle. The indentation may be caused, for example, by a drop-off in light from a middle of the sweep as a result of at least some light reflecting off of the patient tube 106. FIG. 14 illustrates waveforms 1400, which are calculated by the processor 120 by determining a first derivative of the waveforms 1300. Line 1402 represents an average of the waveforms 1400 and may additionally or alternatively be used as a reference waveform for the dry tube state. In the present example, for the dry tube state, the waveforms 1400 show a change in slope between sampled points 25 and 55 that differs from the change in slope in the waveforms 1200 for the same sampled points during sweep periods. The change in slope results from the indentation in the waveforms 1300. As one can appreciate, the significant difference between waveforms 1200 and 1400 between sample points 25 and 55 helps to ensure that a no-tube state and a dry tube state are sufficiently distinct, enabling the processor 120 to make an accurate determination and prevent, for instance, false detections.

Figure 15:
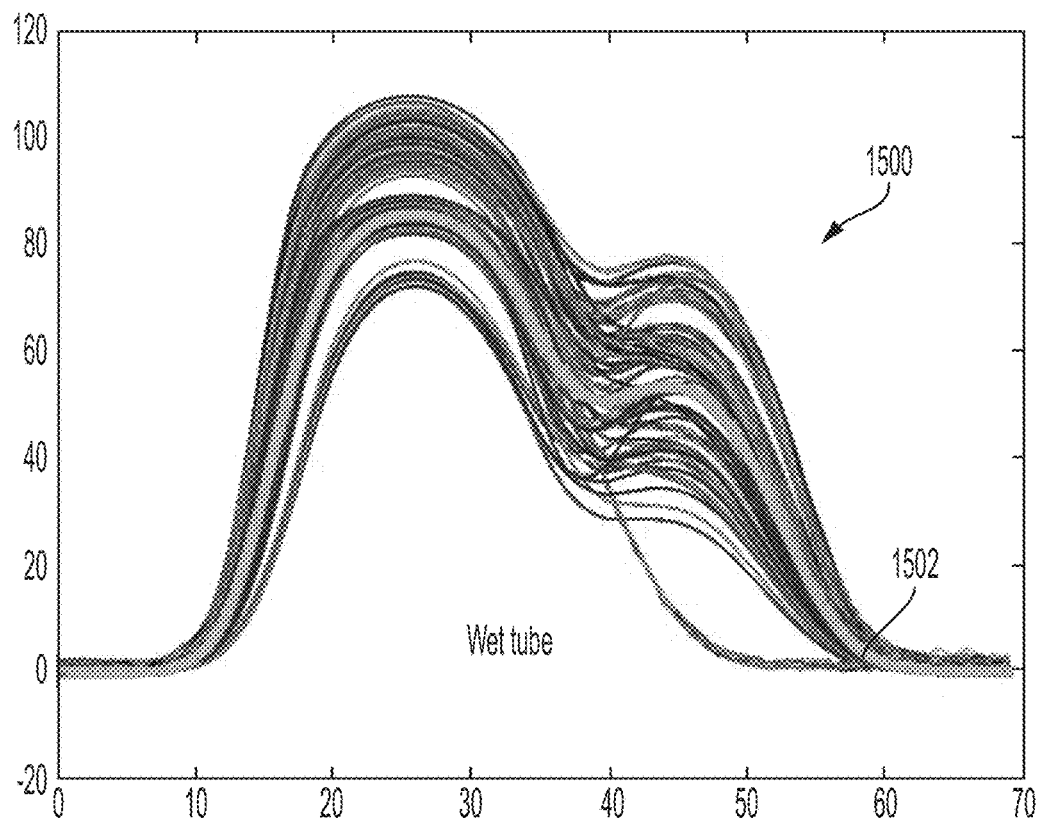
Figure 16:
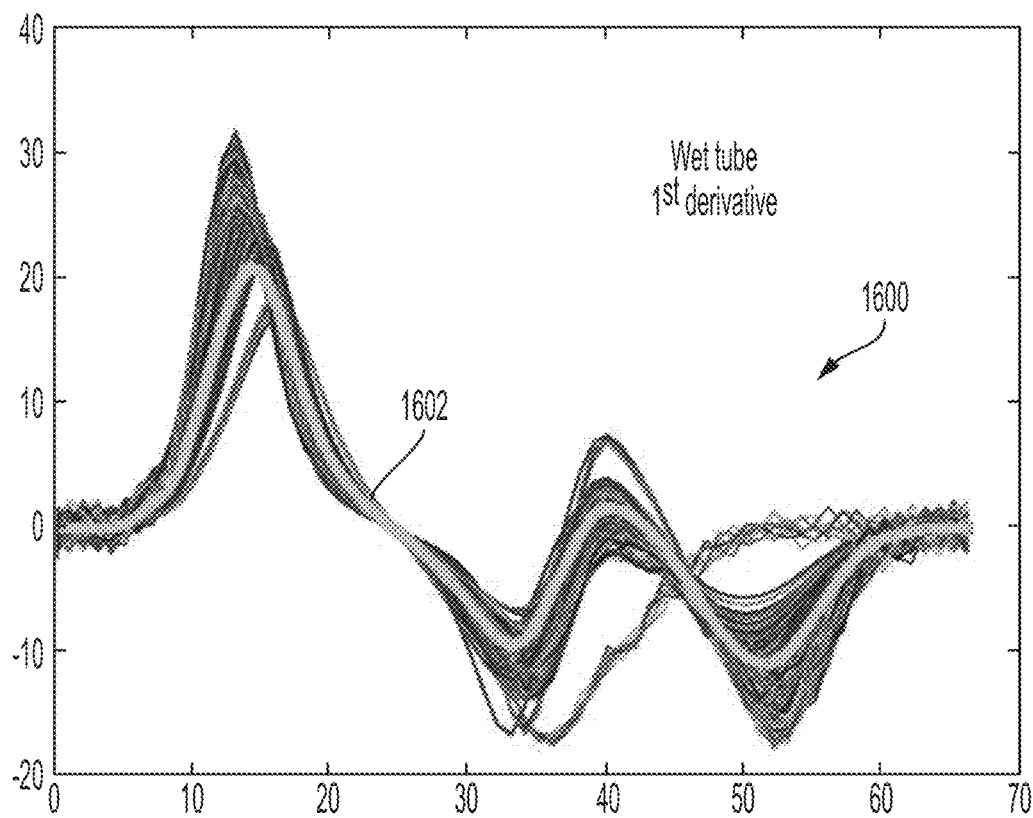

FIG. 15 illustrates a diagram of acquired waveforms 1500 corresponding to a wet tube state. Similar to FIGS. 11 and 13, the acquired waveforms 1500 include about 500 individual waveforms from 500 different sweeps. Line 1502 represents an average of the waveforms 1500 and may be used as a reference waveform for the wet tube state. The waveforms 1500 are similar to the waveform 1300 up unto about sample point 35. After that point, the waveforms 1500 degrade in intensity as fluid absorbs or reflects more light from the second and third emitters 322. FIG. 16 illustrates waveforms 1600, which the processor 120 calculates by determining a first derivative of the waveforms 1500. Line 1602 represents an average of the waveforms 1600 and may additionally or alternatively be used as a reference waveform for the wet tube state. For the wet tube state, the waveforms 1600 show a change in slope between sampled points 25 and 55 that differs from the slope of the waveforms 1200 and 1400. The change in slope results from the degradation in intensity in the waveforms 1400 after point 35. The significant difference between waveforms 1200, 1400, and 1600 between sample points 25 and 55 helps to ensure that a no-tube state, a dry tube state, and a wet tube state are sufficiently distinct, enabling the processor 120 to make an accurate determination and prevent, for instance, false detections.

After determining a derivative waveform from an acquired waveform, the example processor 120 is configured to compare the derivate waveform to reference waveforms to determine a tube state. The example processor 120 may be configured to compare an acquired waveform to reference waveforms that correspond to different tube states. In an example, each of the lines 1202, 1402, and 1602 may be indicative of the reference waveform for the respective tube state. For each derivative of an acquired waveform, the processor 120 is configured to calculate a difference between the derivate waveform and each of the reference waveforms. The processor 120 may then sum or integrate the calculated differences (e.g., areas) to determine which of the differences (e.g., areas) is the smallest. The processor 120 selects the smallest difference (e.g., area) for the identified tube state, which is indicative of which reference waveform best matches the derivative waveform of the acquired output data.

It should be appreciated that the waveforms 1000 to 1600 may be dependent on a number and spacing of the emitters 322 relative to the detector 320. The waveforms 1000 to 1600 may have different shapes and/or amplitudes for less emitters 322 or more emitters 322. Further, the waveforms 1000 to 1600 may have different shapes and/or amplitudes based on a spacing and/or angle between the emitters 322 and/or the detector 320. However, despite different embodiments, the example processor 120 is configured to use reference waveforms (determined from the arrangement and number of emitters 322 and/or detectors 320) for each of the tube states to determine a tube state based on the sampled output data.

Figure 17:
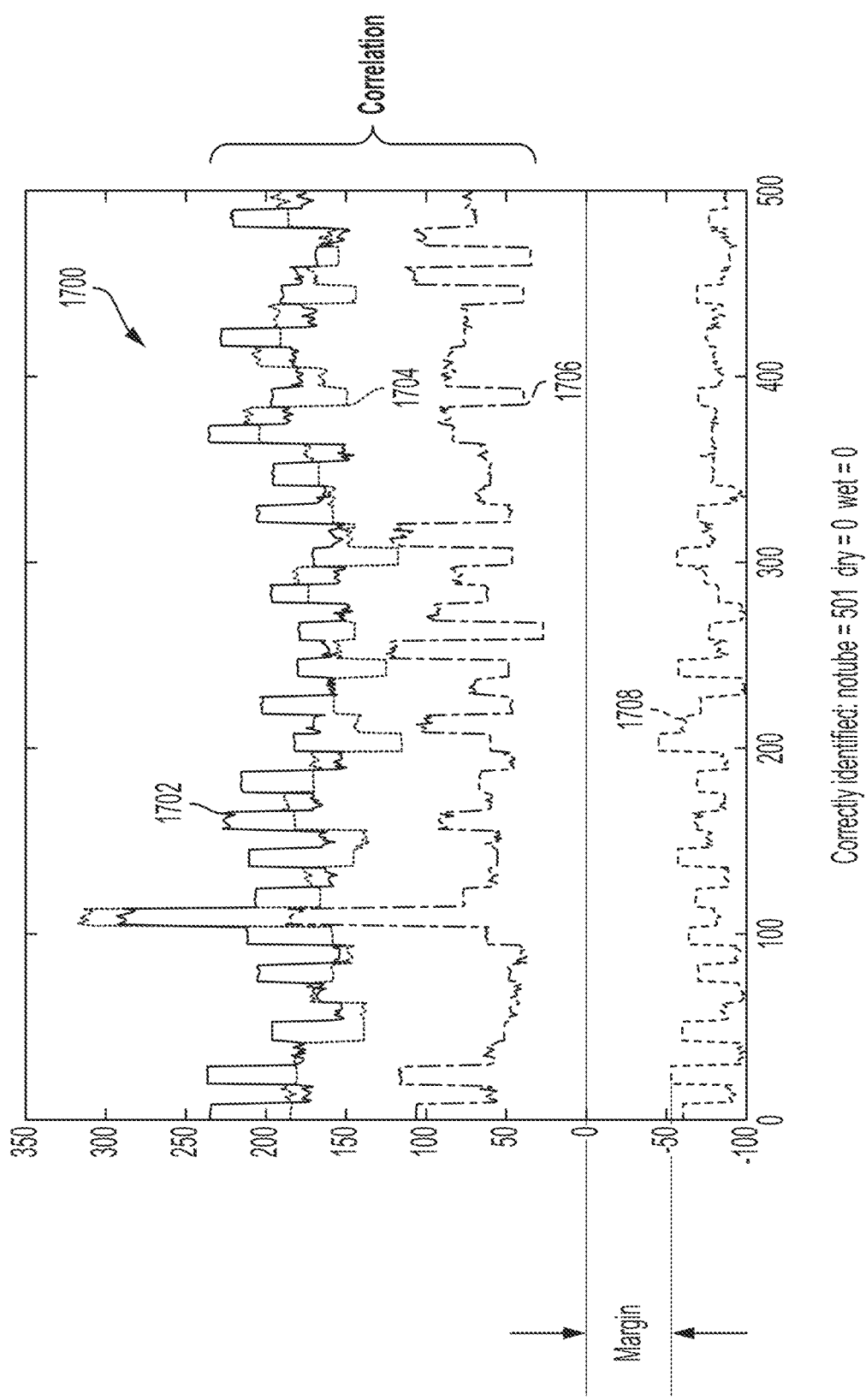
FIGS. 17 to 19 are diagrams that illustrate margins between reference waveforms and the calculated derivate waveforms from FIGS. 11 to 16, according to example embodiments of the present disclosure.
Figure 18:
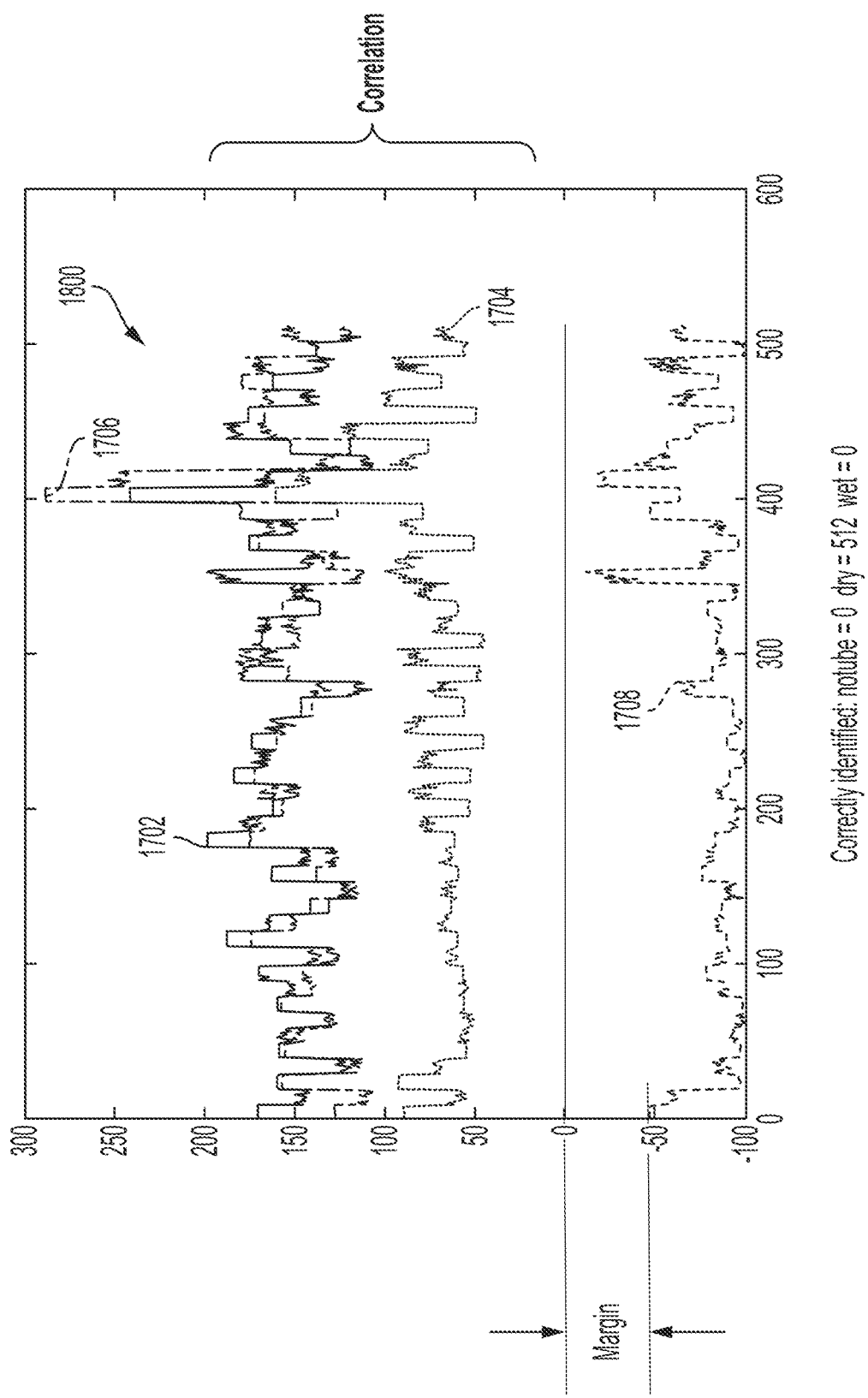
Figure 19:
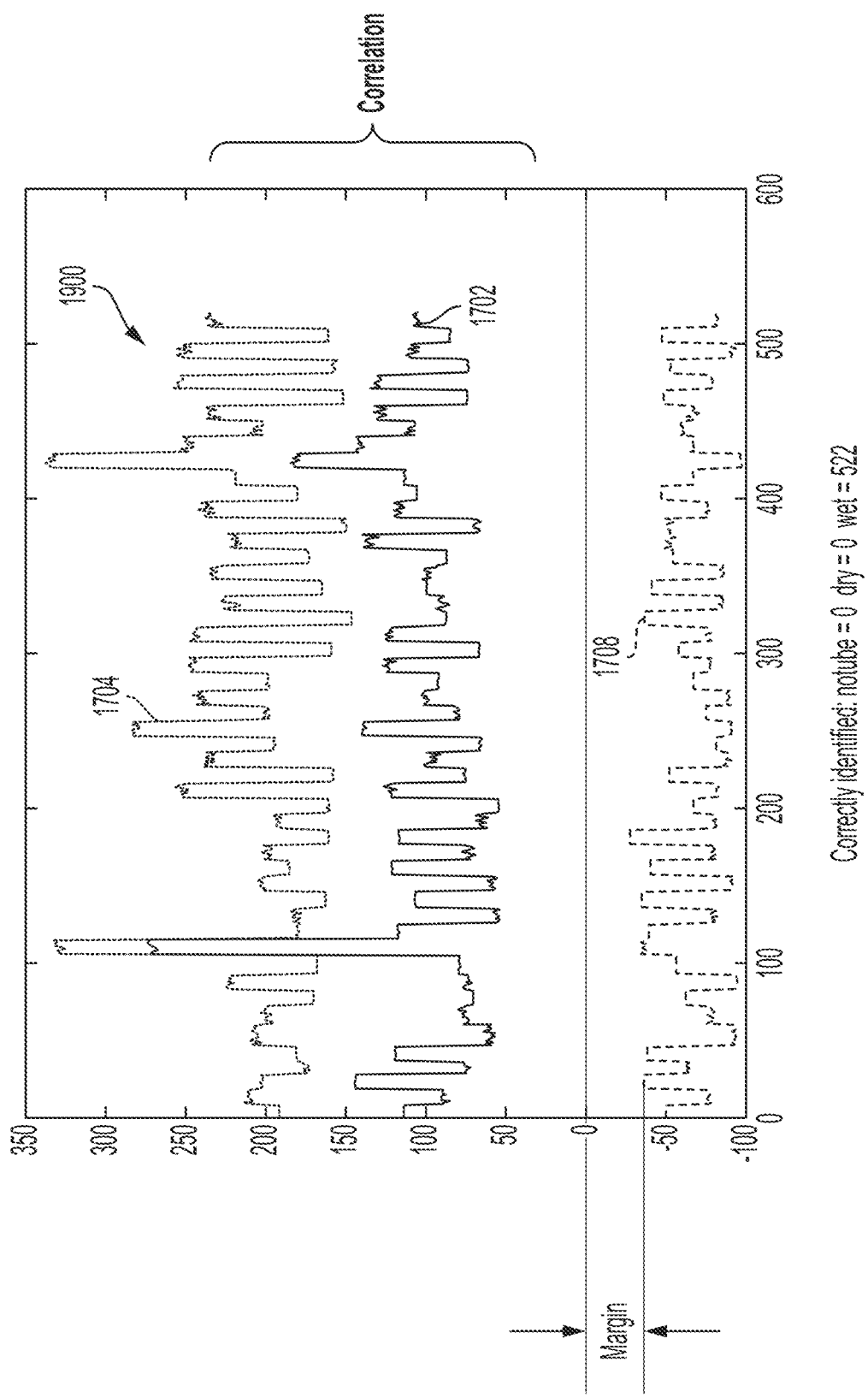

FIGS. 17 to 19 illustrate diagrams illustrative of the margins between the reference waveforms 1202, 1402, and 1602 and the calculated derivative waveforms 1200, 1400, and 1600. FIG. 17 shows each of the five-hundred different no-tube waveforms 1200 as a value between 0 and 500 on the x-axis and an area difference between the waveforms 1200 and each of the reference waveforms 1202, 1402, and 1602 on the y-axis. Line 1702 represents an area difference with the dry tube reference waveform 1402, line 1704 represents an area difference with the wet tube reference waveform 1602, and line 1706 represents an area difference with the no-tube reference waveform 1202. Line 1708 shows a margin between the closest match compared to the next closest match. As shown in FIG. 17, the no-tube state was consistently detected since the waveforms 1200 most closely matched the reference waveform 1202, with at least a 50% margin compared to the next closest match. As such, the processor 120 correctly identified the no-tube state in every instance.

FIG. 18 illustrates that the dry tube reference waveform 1402 most closely matches all five-hundred-twelve waveforms 1400. Although the margin was smaller for some waveforms, there was sufficient difference to enable the processor 120 to select the correct state. FIG. 19 illustrates that the wet tube reference waveform 1602 most closely matched all five-hundred-twenty waveforms 1600. The margin was at least 40% with the dry tube reference waveform 1402. Again, the processor 120 selected the correct tube state.

In some embodiments, the example processor 120 may calculate a Fourier transform of an acquired waveform rather than determining a derivative waveform. The Fourier transform may be compared by the processor 120 to one or more reference waveforms to determine a tube state. In yet other examples, the processor 120 is configured to use Pearson correlation of an acquired waveform to determine a tube state. Further, in some embodiments, the processor 120 is configured to smooth, oversample, and/or filter acquired data to adjust for outlier data. Moreover, in some embodiments, the processor 120 may calculate a confidence of the tube state determination. The tube state may be based on the margin data or how close two reference waveforms are to a derivative of an acquired waveform. The example processor 120 may discard a waveform if the confidence is below a threshold (e.g., 65%) and/or cause an alarm to activate to indicate that a tube state cannot be determined.

In some embodiments, the processor 120 is configured to detect a certain tube state a threshold number of times before determining or indicating that the detected tube state is valid. Such a configuration reduces the chances of an erroneous tube state detection affecting operation of the medical fluid delivery system 100. The threshold may be between 5 detections and 20 detections within a time period (e.g., 5 seconds, 10 seconds, 30 seconds, 1 minute, 2 minutes, etc.) and/or 5 to 20 detections out of a possible 7 to 25 detections. In an example, the processor 120 may be in a no-tube state. Upon insertion of the patient tube 106 into the priming sensor 104, the processor 120 begins to accumulate detections of the dry tube state as sweep patterns are operated. After a threshold number of detections of the dry tube state are made within a time period or within a specified number of detections, the processor 120 validates that the dry tube state is present and transmits the appropriate message/instruction.

In some embodiments, the processor 120 may omit certain reference waveforms used in a comparison. For example, if the processor 120 is in a no-tube state, the processor 120 generally does not detect a wet tube state as a next transition. As such, in a no-tube state, the processor 120 may omit reference waveforms associated with a wet tube state to reduce false state detections.

Figure 20:
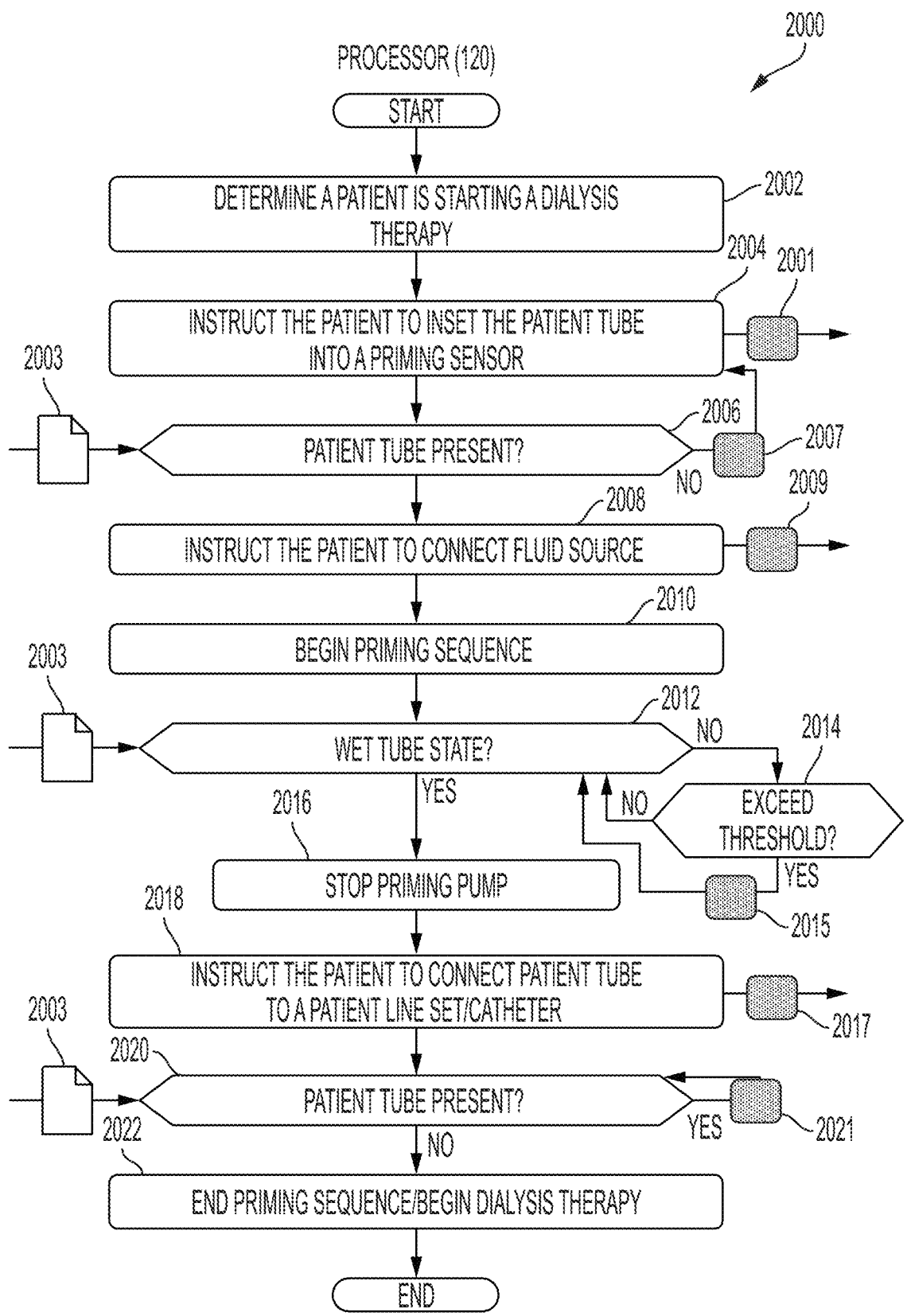
FIG. 20 is a diagram of an example procedure to determine a tube state of a patient tube, according to an example embodiment of the present disclosure.

FIG. 20 illustrates a diagram of an example procedure 2000 to determine a tube state of the patient tube 106 of FIG. 1, according to an example embodiment of the present disclosure. The example processor 120 is configured to execute or operate machine-readable instructions that are described by the procedure 2000. Although the procedure 2000 is described with reference to the flow diagram illustrated in FIG. 20, it will be appreciated that many other methods of performing the acts associated with the procedure 2000 may be used. For example, the order of many of the blocks may be changed, certain blocks may be combined with other blocks, and many of the blocks described are optional. For example, any of blocks 2808, 2810, and 2812 may be omitted.

Figure 21:
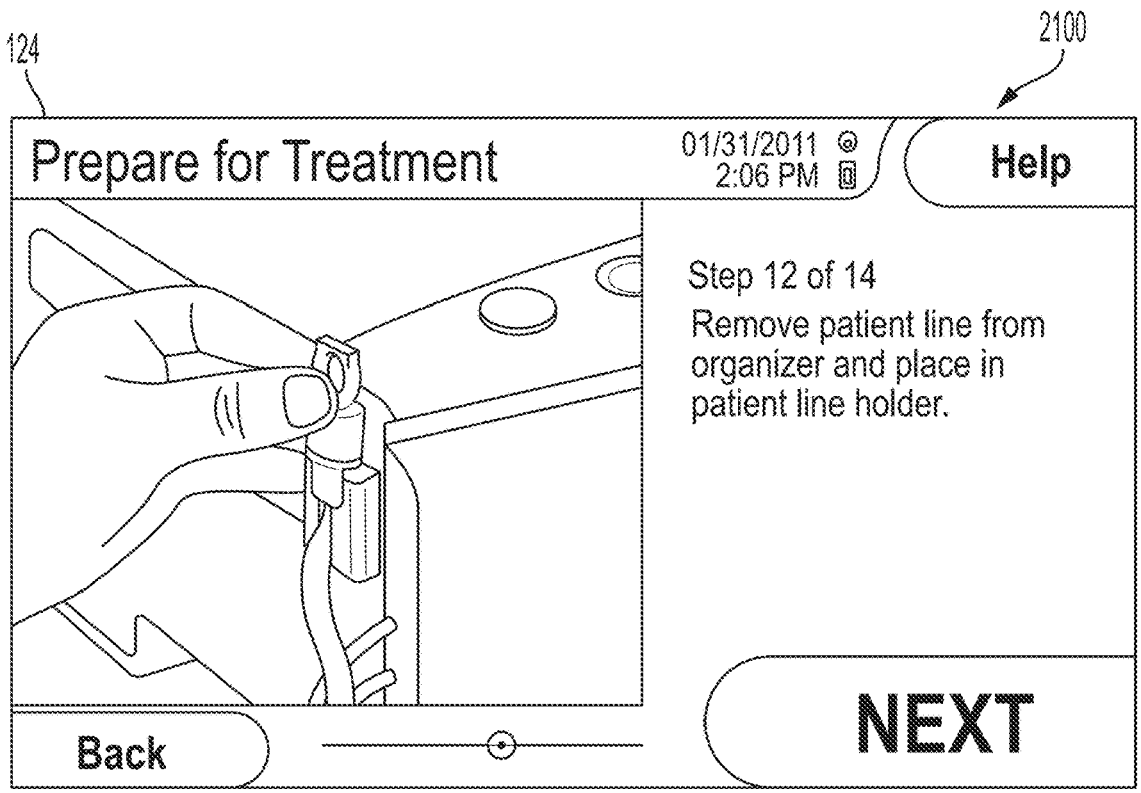
FIGS. 21 to 27 are diagrams of graphics that may be displayed by a dialysis machine to assist a patient in performing a priming procedure in preparation of a dialysis therapy, according to example embodiments of the present disclosure.

To begin, the example processor 120 receives an indication or determines that a patient is to start a dialysis therapy (block 2002). The example processor 120 may receive an input via the user interface 124 that a patient has selected to begin a therapy. Alternatively, the processor 120 may determine via an electronically stored schedule that a patient is to undergo a dialysis therapy. To prepare for the therapy, the example processor 120 operates a setup routine in one embodiment, which may include connecting tubes to appropriate containers and performing a priming and/or disinfecting procedure. When it is time to prime the patient tube 106, the example processor 120 transmits a message 2001 for display that the patient is to inset the patient tube 106 into the priming sensor 104 (block 2004). FIG. 21 illustrates an example graphic 2100 that may be displayed by the user interface 124 based on the message 2001. The graphic 2100 includes text and an illustration regarding how the patient tube 106 is to be placed within the priming sensor 104.

Figure 22:
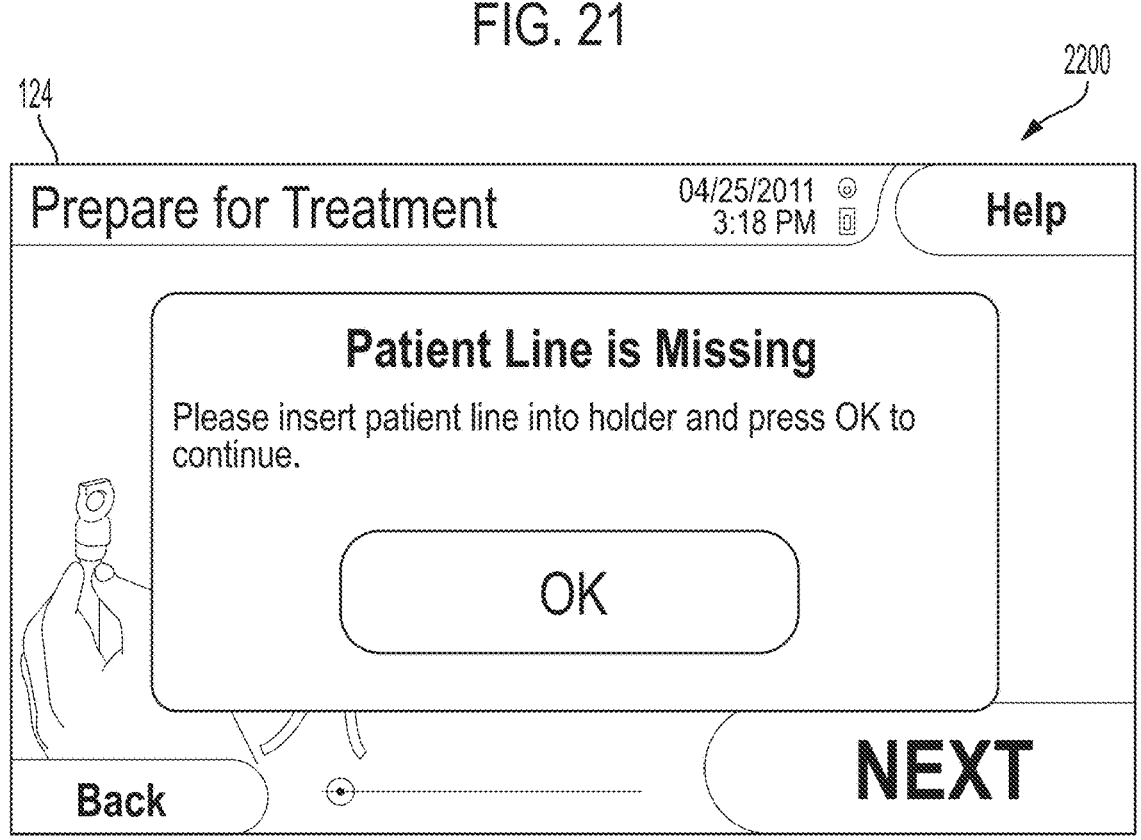

To determine if the patient correctly inserted the tube 106 into the priming sensor 104, the example processor 120 is configured to perform one or more sweep patterns to determine a tube state (block 2006). For each sweep pattern performed, the processor 120 receives sampled output data 2003, which is processed into an acquired waveform and used to determine a tube state, as discussed above in connection with FIGS. 7 to 19. If the no-tube state is detected, the processor 120 is configured to transmit one or more messages 2007 indicative that the patient tube 106 is missing. FIG. 22 illustrates a diagram of a graphic 2200 that may be displayed by the user interface 124 based on the message 2007. The graphic 2200 includes a pop-up window alerting the patient that the patient tube 106 has not been inserted.

Figure 23:
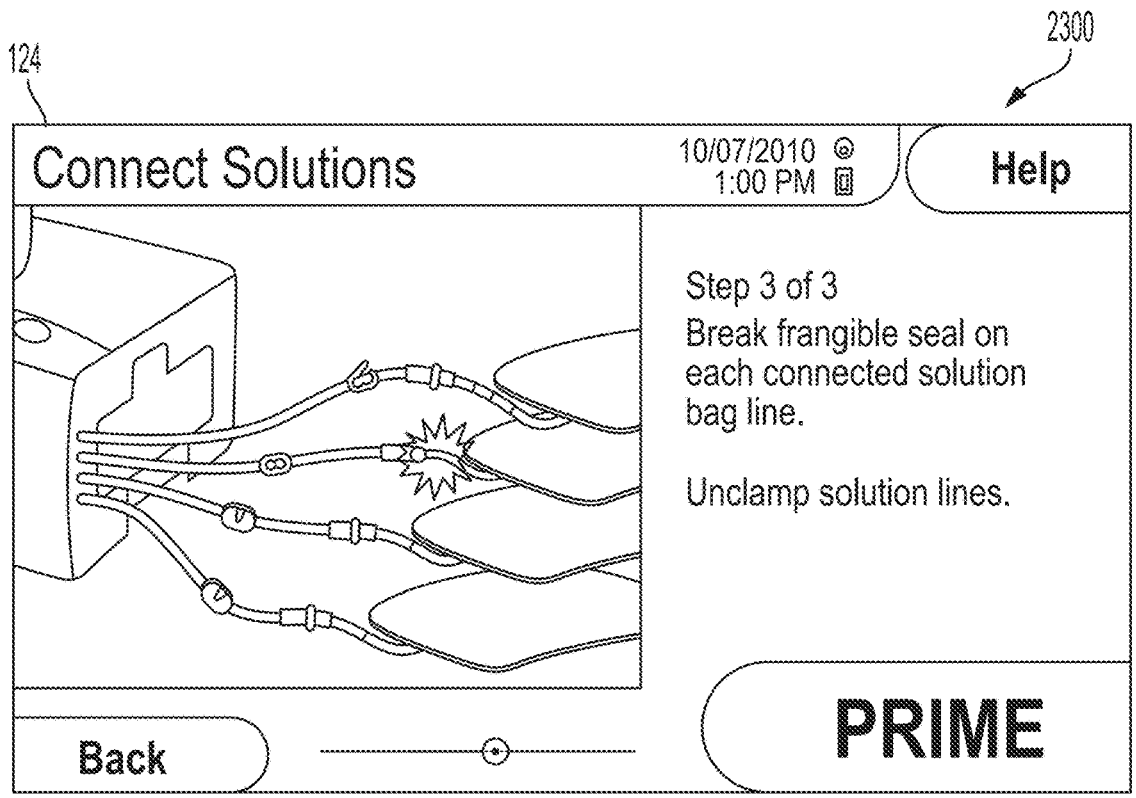
Figure 24:
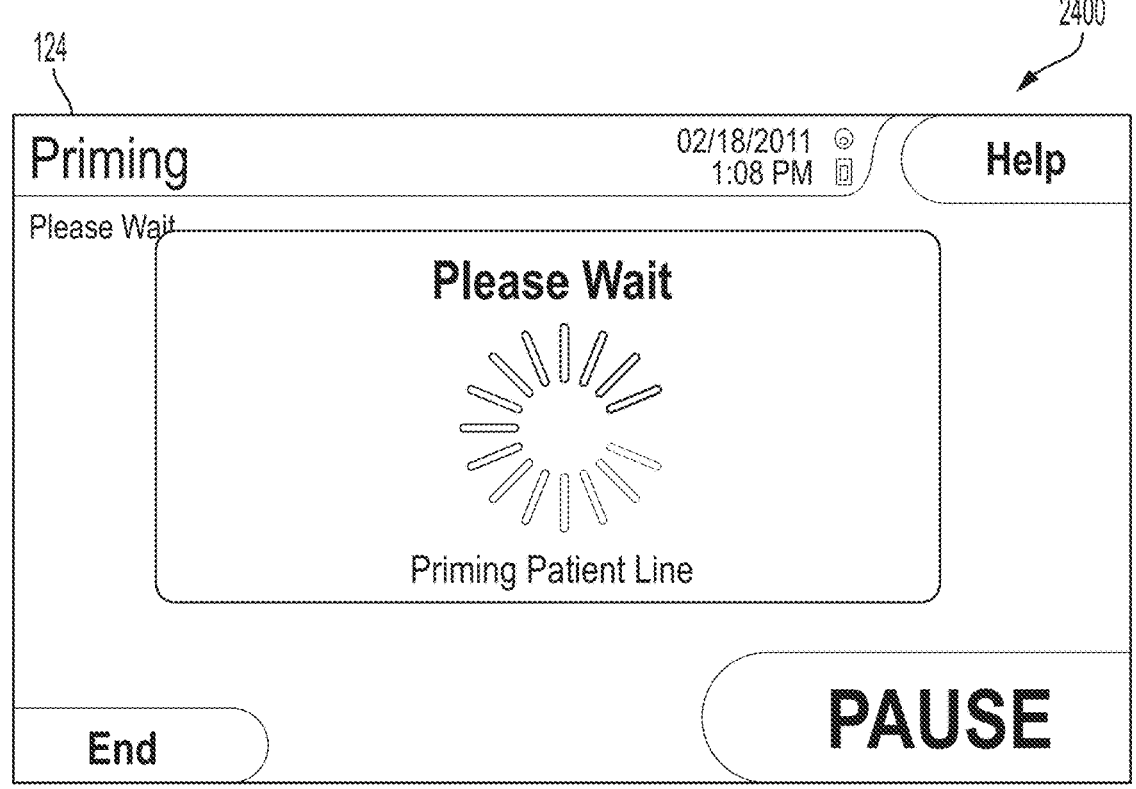

If a dry tube state is detected, the example processor 120 transmits one or more messages 2009 indicative that the patient is to connect a tube to a fluid source (block 2008). In other embodiments, the message 2009 may instruct a patient to begin a priming sequence. FIG. 23 shows a diagram of a graphic 2300 that may be displayed by the user interface 124 based on the message 2009. The graphic 2300 includes text and images regarding how a fluid source is to be connected to one or more source tubes of a dialysis machine. After the patient has connected the tubes, the patient may select the priming button shown in the graphic 2300. Selection of the priming button provides an indication for the processor 120 to begin a priming sequence (block 2010). The priming sequence includes causing at least one pump 110 to move dialysis fluid from at least one source container to the patient tube 106. During this sequence, the processor 120 receives sampled output data 2003 from performing multiple sweeps of emitters 322 (block 2012). In addition, during this sequence, the processor 120 may cause the graphic 2400 of FIG. 24 to be displayed on the user interface 124 indicating that a priming sequence is being run.

Figure 25:
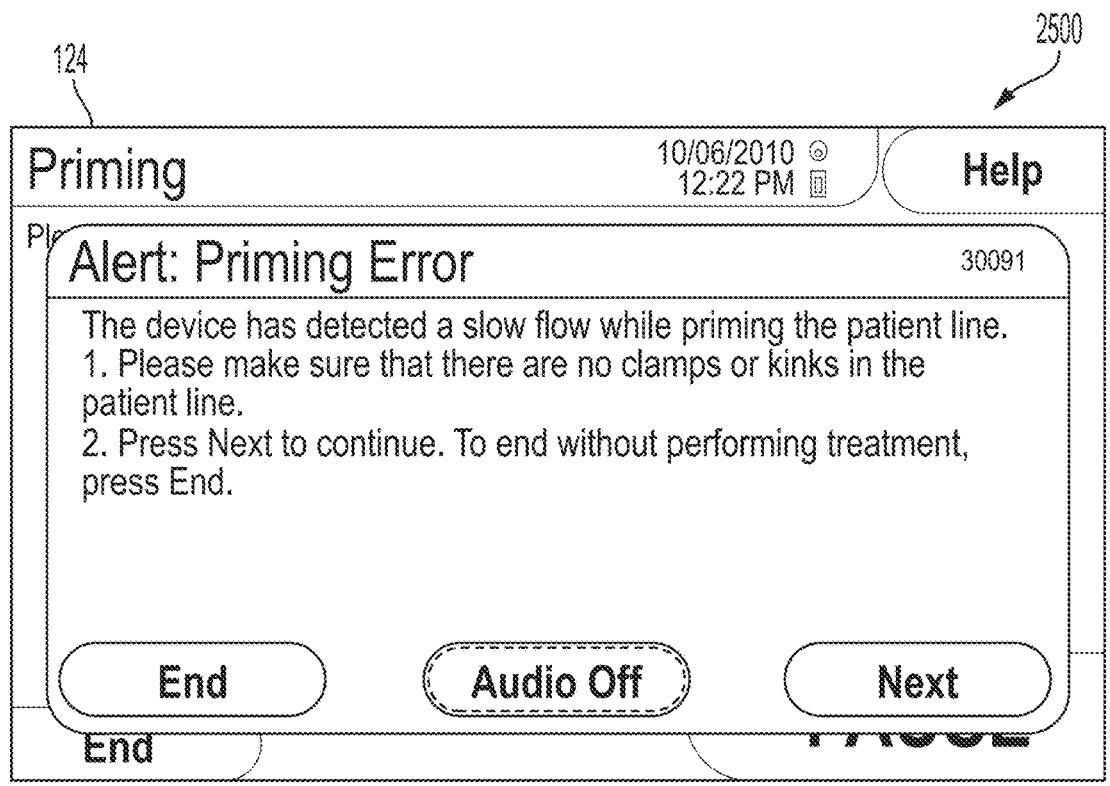

For each detection of a dry tube state, the processor 120 may update or increment a threshold counter and determine whether the counter exceeds a time threshold/limit (block 2014). If the time threshold is exceeded, the patient tube 106 is not able to prime within an expected time period and may have an occlusion, leak, constriction, or other condition that is preventing dialysis fluid from filling the tube. In an attempt to correct the situation, the processor 120 is configured to transmit one or more messages 2015, which causes graphic 2500 of FIG. 25 to be displayed. In addition, an alarm may be activated. The graphic 2500 includes text indicative of the priming error and instructions for the patient to check the tubes from the source fluid and the patient tube 106. After a patient has identified and corrected the issue with the tubes, the patient may select the next button to re-start the priming sequence.

Figure 26:
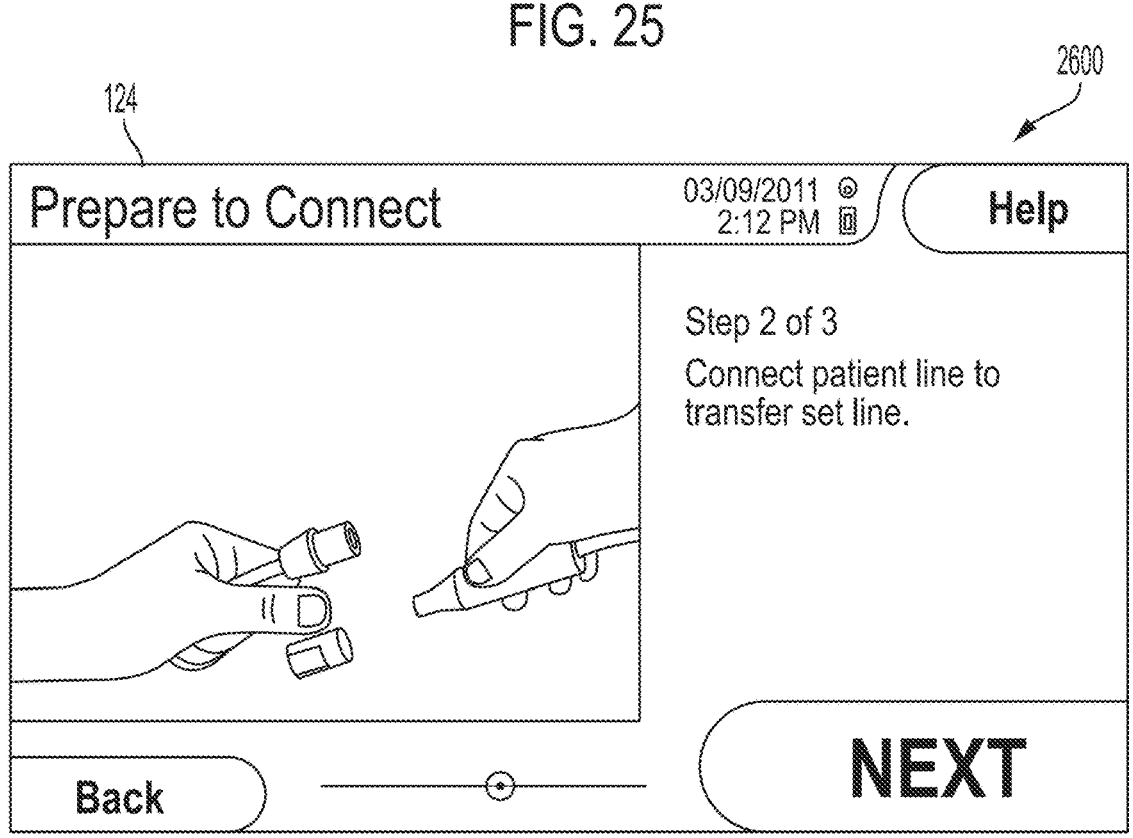

Returning to block 2012, if a wet tube state is detected, the example processor 120 may be configured to stop the priming pump 110 (block 2016). In some embodiments, the example processor 120 is configured to confirm that the prime has been correctly performed. The example processor 120 may also transmit one or more messages 2017 instructing the patient to connect the patient tube 106 to a patient line set and/or catheter to begin treatment (block 2018). FIG. 26 illustrates a diagram of a graphic 2600 that may be displayed by the user interface 124 based on the message 2017. The graphic 2600 includes text and an image providing a patient information regarding how to connect the patient tube 106 to a line set or catheter.

Figure 27:
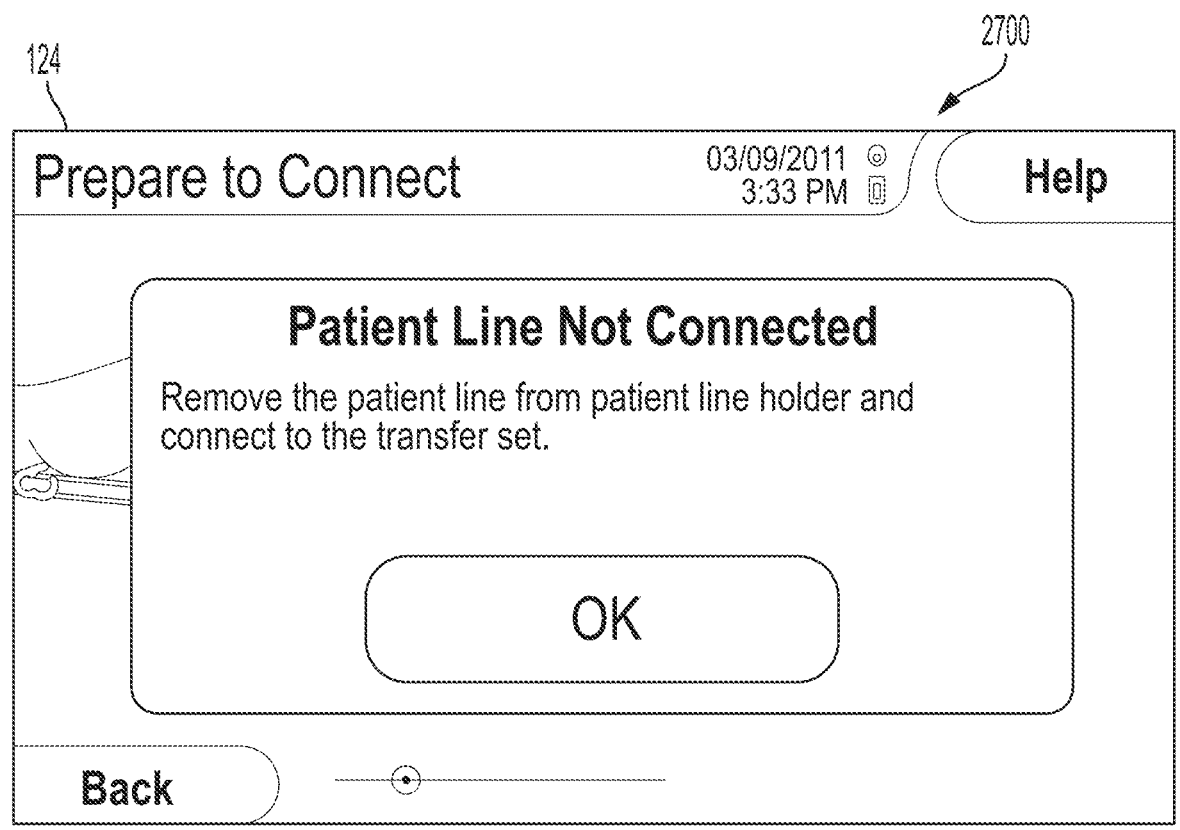

The example processor 120 is configured to use the priming sensor 104 to determine if the patient tube 106 is still present in the sensor (block 2020). The processor 120 receives one or more sets of sampled output data 2003 to determine if the tube is still in the priming sensor 104. If the tube is still present, the processor 120 transmits one or more messages 2021 indicative that the patient is to remove the tube from the priming sensor 104. FIG. 27 illustrates a diagram of a graphic 2700 that may be displayed by the user interface 124 based on the message 2021. The graphic 2700 includes a pop up window providing a warning that that the patient tube has not been removed from the priming sensor for connection to a line set or catheter. If the patient tube 106 is no longer detected, the example processor 120 is configured to end the priming sequence and/or enable the dialysis therapy to begin (block 2022). The example procedure 2000 then ends.

Figure 28:
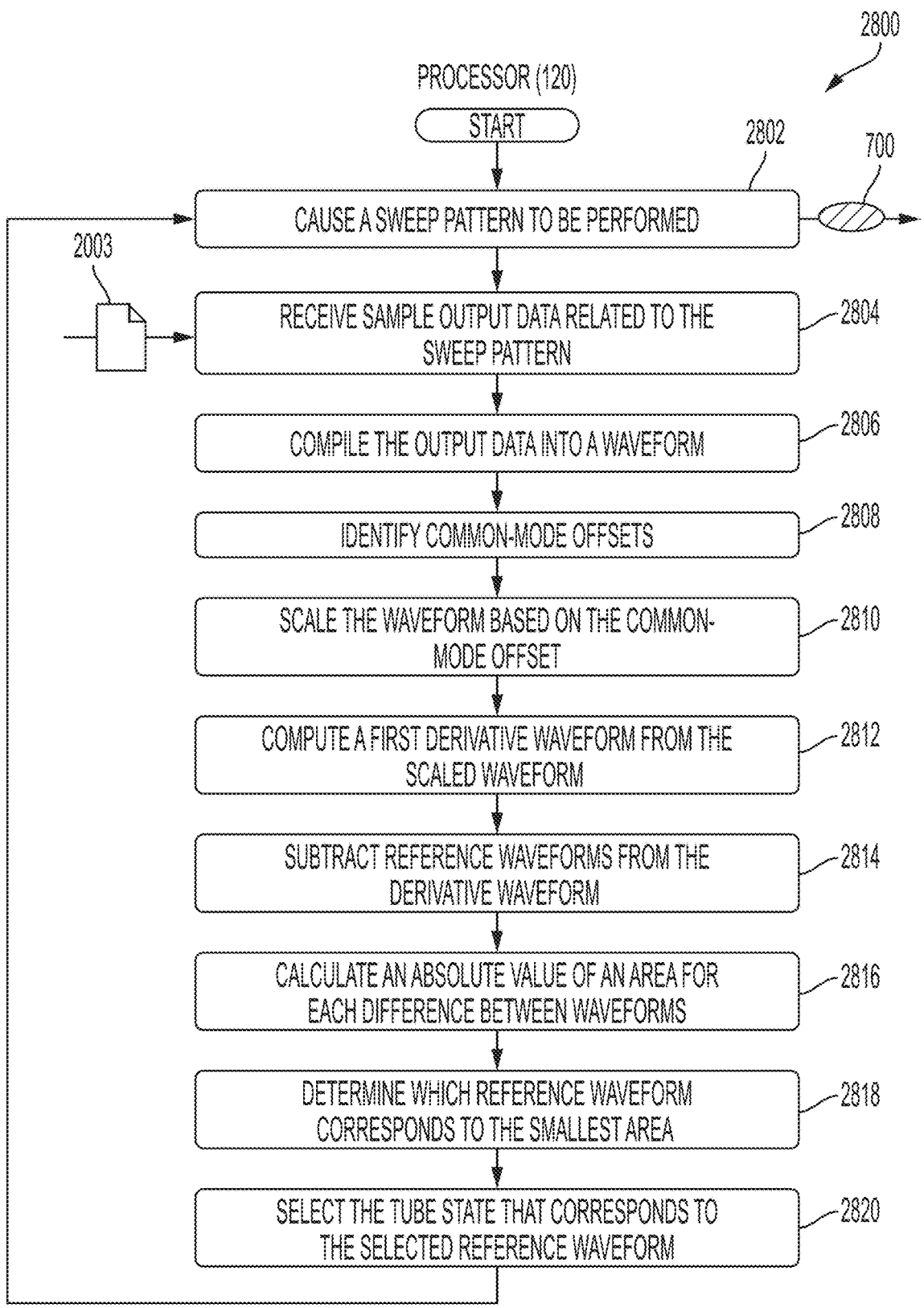
FIG. 28 is a diagram of an example procedure configured to determine a tube state of a patient tube, according to an example embodiment of the present disclosure.

FIG. 28 shows a diagram of an example procedure 2800 configured to determine a tube state of the patient tube 106, according to an example embodiment of the present disclosure. The example processor 120 is configured to execute or operate machine-readable instructions that are described by the procedure 2800. Although the procedure 2800 is described with reference to the flow diagram illustrated in FIG. 28, it will be appreciated that many other methods of performing the acts associated with the procedure 2800 may be used. For example, the order of many of the blocks may be changed, certain blocks may be combined with other blocks, and many of the blocks described are optional.

The example procedure 2800 begins when the processor 120 performs a priming sequence and causes a sweep pattern 700 to be performed by the priming sensor 104 during a sweep period (block 2802). While the sweep pattern 700 is performed by the priming sensor 104, the example processor 120 receives sampled output data 2003 from the priming sensor 104 (block 2804). The data 2003 is indicative of detected light brightness at the detector 320 while the sweep pattern 700 is performed at the priming sensor 104. The example processor 120 compiles, combines, or aggregates the sampled output data into a waveform or spatial array curve (block 2006).

The example processor 120 performs one or more of the following operations on the array curve to identify a tube state. For instance, the processor 120 may identify common-mode offsets within the spatial array curve (block 2808). The common-mode offsets may be caused by ambient light effects on the detector 320. The processor 120 may also scale the array curve to remove the common-mode offset to normalize the curve shape but retain the amplitude data (block 2010).

The example processor 120 may additionally or alternatively compute a first derivative waveform from the scaled (or un-scaled) array curve or waveform (block 2812). The processor 120 then determines a difference between the derivative waveform and reference waveforms that correspond to the possible tube states (block 2814). Subtracting the waveforms may include determining a difference in amplitude between the waveforms at each of the sample points that correspond to the sweep pattern. The processor 120 calculates an absolute value of an area of the determined difference for each of the reference waveforms (block 2816). The processor 120 compares the areas to determine a smallest area, and determines which reference waveform is associated with the smallest area (block 2818). The processor 120 then selects the tube state that corresponds to the selected reference waveform and transmits one or more messages indicative of the determined tube state (block 2820).

The processor 120 in some embodiments may determine a confidence or margin of the determined result. If the confidence or margin is below a threshold, the processor 120 may discard the result and/or transmit an error message indicative that the tube state cannot be determined. In some instances, the processor 120 may update a counter that tracks a number of times each tube state has been detected. If a threshold is met or exceeded, the processor 120 may transmit an error indicative of an issue with the priming sequence or a message instructing a patient to check an insertion of a patient tube into the priming sensor 104. The example procedure 2800 returns to block 2802 to repeatedly determine the tube state by causing additional sweep patterns to be performed by the priming sensor 104.

CONCLUSION

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A peritoneal dialysis apparatus comprising:
   a patient tube configured to receive dialysis fluid from a source of dialysis fluid;
   at least one pump configured to move dialysis fluid from the source to the patient tube;
   a priming sensor including a first emitter, a second emitter, a third emitter, and a detector, the detector configured to detect light, emitted by the first emitter, the second emitter, and the third emitter, that interacts with the patient tube;
   a processor configured to operate the priming sensor; and
   a memory storing instructions, which when executed by the processor, cause the processor to:
   (i) cause the first emitter, the second emitter, and the third emitter to operate in a sweep pattern during a sweep period by:
      at a first time, causing the first emitter to emit light during a first time period according to an activation pattern that is defined by instructions in the memory,
      at a second time during or after the first time, causing the second emitter to emit light during a second time period according to the activation pattern, and
      at a third time during or after the second time, causing the third emitter to emit light during a third time period according to the activation pattern, where a peak brightness of the first emitter occurs before a peak brightness of the second emitter, and the peak brightness of the second emitter occurs before a peak brightness of the third emitter,
   wherein the activation pattern specifies a control of a brightness of the light emitted by the first, second, and third emitters by increasing a duty cycle from a start of a respective time period until half of the respective time period where the peak brightness is reached, and decreasing the duty cycle from half of the respective time period until the end of the respective time period,
   (ii) receive output data from the detector that is indicative of light detected during the sweep period,
   (iii) create an output waveform corresponding to the sweep period based on the output data,
   (iv) compare the output waveform to at least one reference waveform to determine one of (a) a no-tube state, (b) a dry tube state, or (c) a wet tube state, and
   (v) provide an output indicative of the comparison.

2. The apparatus of claim 1, wherein the processor is further configured such that when the wet tube state is determined, a message indicative of the wet tube state is transmitted, and
   wherein (i) to (iv) are repeated during a priming sequence while the least one pump is caused to move the dialysis fluid from the source to the patient tube until the wet tube state is determined.

3. The apparatus of claim 1, wherein the processor is further configured such that when the wet tube state is determined, a peritoneal dialysis treatment is enabled.

4. The apparatus of claim 1, wherein the processor is configured to:
   determine an analytical output waveform by calculating a derivative of the output waveform; and compare the analytical output waveform to the at least one reference waveform to determine one of the states (a) to (c).

5. The apparatus of claim 1, which includes at least three reference waveforms, wherein the processor is configured to match one of the reference waveforms to the output waveform to determine the states (a) to (c).

6. The apparatus of claim 1, which includes a user interface configured to display at least one of text or a graphic corresponding to the determined state (a) to (c).

7. The apparatus of claim 1, wherein the processor and the detector cooperate to acquire between ten and one-hundred samples to form the output data indicative of the detected light during the sweep period.

8. The apparatus of claim 1, wherein the processor is further configured to:
   increment a counter each time the wet tube state is determined;
   compare a value of the counter to a counter threshold; and
   determine the wet tube state when the value of the counter equals or exceeds the counter threshold.

9. The apparatus of claim 8, wherein the counter threshold is between two and ten.

10. The apparatus of claim 1, wherein the second time begins between halfway through and ¾ of the way through the first time period, and the third time begins between halfway through and ¾ of the way through the second time period.

11. The apparatus of claim 1, wherein the activation pattern corresponds to a Gaussian impulse waveform.

12. The apparatus of claim 1, wherein the first emitter is located on a first side of the patient tube opposite from the detector which is located on a second side of the patient tube when the patient tube is inserted into the priming sensor.

13. The apparatus of claim 12, wherein the second emitter is located on the first side of the patient tube adjacent to the first emitter, and the third emitter is located adjacent to the second emitter and is aligned to direct light between 30 and 60 degrees relative to light emitted from the first emitter and the second emitter.

14. The apparatus of claim 1, wherein the first emitter is positioned to be a transmissive light emitting diode relative to the detector, the second emitter is positioned to be an intermediate light emitting diode relative to the detector, and the third emitter is positioned to be a reflective light emitting diode relative to the detector.

15. The apparatus of claim 1, wherein the priming sensor includes at least one retainer section configured to retain the patient tube within the priming sensor.

16. A peritoneal dialysis apparatus comprising:
   a priming sensor including a first emitter, a second emitter, a third emitter, and a detector, the detector configured to detect light emitted by the first emitter, the second emitter, and the third emitter through a dialysis tube;
   a processor configured to operate the priming sensor; and
   a memory storing instructions, which when executed by the processor, cause the processor to:
   (i) cause the first emitter and the second emitter to operate in a sweep pattern during a sweep period by:
      at a first time, causing the first emitter to emit light during a first time period according to an activation pattern that is defined by instructions in the memory,
      at a second time during or after the first time, causing the second emitter to emit light during a second time period according to the activation pattern, and
      at a third time during or after the second time, causing the third emitter to emit light during a third time period according to the activation pattern,
      wherein the activation pattern specifies a control of a brightness of the light emitted by the first, second, and third emitters by increasing a duty cycle from a start of a respective time period until half of the respective time period where a peak brightness is reached, and decreasing the duty cycle from half of the respective time period until the end of the respective time period,
   (ii) receive output data from the detector that is indicative of light detected during the sweep period,
   (iii) create an array curve corresponding to the sweep period based on the output data,
   (iv) determine a state of the dialysis tube based on the array curve, the state including at least one of (a) a no-tube state, (b) a dry tube state, and (c) a wet tube state, and
   (v) when the wet tube state is determined, transmit a message indicative that the dialysis tube is primed.

17. The apparatus of claim 16, wherein the processor is configured to determine the state of the dialysis tube by:
   (I) removing common-mode offsets of the array curve to exclude ambient light effects;
   (II) scaling the array curve based on the common mode offsets to normalize a shape of the array curve;
   (III) computing a first derivative of the scaled array curve;
   (IV) subtracting a reference curve for each of the three states from the first derivative of the scaled array curve;
   (V) calculating an absolute value of an area for each of the three reference curves from (IV); and
   (VI) determining the state of the dialysis tube by selecting the reference curve that corresponds to a smallest absolute value from (V).

* * * * *